United States Patent [19]

Charpentier

[11] Patent Number: 5,547,983
[45] Date of Patent: Aug. 20, 1996

[54] AROMATIC AND POLYCYCLIC COMPOUNDS AND THEIR USE IN HUMAN OR VETERINARY MEDICINE AND IN COSMETICS

[75] Inventor: Bruno Charpentier, Biot, France

[73] Assignee: Centre International de Recherches Dermatologiques Galderma (CIRD Galderma), Valbonne, France

[21] Appl. No.: 140,079

[22] PCT Filed: May 4, 1992

[86] PCT No.: PCT/FR92/00404

§ 371 Date: Aug. 22, 1994

§ 102(e) Date: Aug. 22, 1994

[87] PCT Pub. No.: WO92/19583

PCT Pub. Date: Nov. 12, 1992

[30] Foreign Application Priority Data

May 2, 1991 [FR] France ................................. 91 05394

[51] Int. Cl.$^6$ ..................... C07C 65/26; C07C 65/17; C07C 63/44
[52] U.S. Cl. ..................... 514/535; 514/543; 514/563; 514/568; 514/569; 424/60; 344/172; 549/447; 549/561; 560/56; 560/42; 560/37; 560/256; 562/452; 562/455; 562/467; 568/646
[58] Field of Search ................................. 560/37, 42, 56, 560/256; 562/452, 455, 467; 514/535, 543, 563, 568, 564; 424/60; 544/172; 549/447, 561; 568/646

[56] References Cited

U.S. PATENT DOCUMENTS 4,801,616  1/1989  Gapinski ................. 514/381

FOREIGN PATENT DOCUMENTS 0199636  10/1986  European Pat. Off. .
0315537   5/1989  European Pat. Off. .

OTHER PUBLICATIONS

Lehman, Cancer Res. 51(18) 4804 (1991).

*Primary Examiner*—Robert Gerstl
*Attorney, Agent, or Firm*—Cushman Darby & Cushman, L.L.P.

[57] ABSTRACT

Aromatic bicyclic compounds of formula (I)

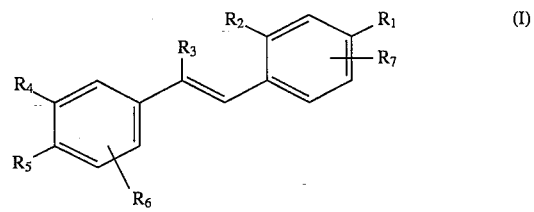

where $R_1$ is specifically —H, $CH_3$, —$CH_2OH$, —OH, —CHO, —$CONH_2$, —COOH, —COOalkyl, —SH, S-alkyl, etc. . . . ; $R_2$ is H; $R_3$ is H, aryl, aralkyl or lower alkyl optionally substituted by a hydroxyl, a lower alkoxy or a —CO—$R_{12}$, $R_{12}$ being specifically H, lower alkyl, hydroxyl, lower alkoxy, or $R_2$ and $R_3$ together form a naphthalene ring with the benzene ring; $R_4$ is a linear branched or unbranched alkyl having 1 to 15 carbon atoms or a cycloaliphatic radical; $R_5$ represents specifically —$(CH_2)_n$—$R_{13}$, —CH=CH—$(CH_2)_n$—$R_{13}$, n being 0 or 1 to 6, $R_{13}$ representing —$COR_{15}$, monohydroxyalkyl, polyhydroxyalkyl, epoxy lower alkyl or —O—CO—$R_{16}$, $R_{15}$ representing specifically —OH, —Oalkyl, —Oaryl, $R_{16}$ being specifically H, lower alkyl, aryl, or aralkyl; $R_6$ and $R_7$ are H, a halogen, lower alkyl or —$OR_{16}$; and also the salts of the compounds of formula (I) in which $R_1$ represents a carboxylic acid grouping; and the chiral analogues of the said compounds of formula (I).

15 Claims, No Drawings

AROMATIC AND POLYCYCLIC COMPOUNDS AND THEIR USE IN HUMAN OR VETERINARY MEDICINE AND IN COSMETICS

This application a 371 of PCT/FR 92/00404 filed May 4, 1992.

The subject of the present invention is new aromatic polycyclic derivatives, process for preparing them and their use in human and veterinary medicine and in cosmetics.

These new compounds find application in the topical and systemic treatment of dermatological conditions linked to a keratinization disorder (differentiation-proliferation) and of dermatological conditions, or the like, with inflammatory and/or immunoallergic components and in connective tissue degeneration diseases, and they have an antitumour activity. In addition, these compounds can be used in the treatment of atopy, whether cutaneous or respiratory, and of rheumatoid psoriasis. They also find application in the ophthalmological field, especially in the treatment of corneopathies.

The compounds according to the invention may be represented by the following general formula:

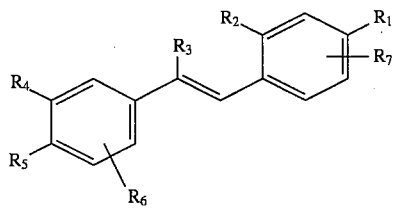

in which:

$R_1$ represents
- (i) a hydrogen atom,
- (ii) the radical —$CH_3$,
- (iii) the radical —$CH_2$—O—$R_8$, $R_8$ representing a hydrogen atom or a lower alkyl radical,
- (iv) a radical —$OR_8$,
- (v) a radical

$R_{10}$ representing:
- a) a hydrogen atom,
- b) a radical

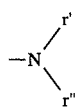

r' and r" representing a hydrogen atom, a lower alkyl radical, a mono- or polyhydroxyalkyl radical, an optionally substituted aryl radical or an amino acid or sugar residue or alternatively, taken together, form a heterocycle,
- (c) a radical —$OR_{11}$ $R_{11}$ representing a hydrogen atom, a linear or branched alkyl radical having 1 to 20 carbon atoms, a mono- or polyhydroxyalkyl radical, an aryl or aralkyl radical which is (are) optionally substituted or a sugar residue or an amino acid residue, and
- (vi) a radical —$S(O)_t R_8$, t being 0, 1 or 2 and $R_8$ being as defined above, $R_2$ represents a hydrogen atom, $R_3$ represents a hydrogen atom, an aryl radical, an aralkyl radical or a lower alkyl radical optionally substituted by a hydroxyl, by a lower alkoxy or by a radical

$R_{12}$ representing a hydrogen atom, a low alkyl radical, a hydroxyl radical, a lower alkoxy radical or a radical

r' and r" having the same meanings as above, or $R_2$ and $R_3$, taken together, form, with the benzene nucleus, a naphthalene nucleus, $R_4$ represents a linear or branched alkyl radical having 1 to 15 carbon atoms or a cycloaliphatic radical, $R_5$ represents the radical —$(CH_2)_n$—$R_{13}$, the radical —CH=CH—$(CH_2)_n$—$R_{13}$, or the radical —$O(CH_2)_m$—$R_{14}$ n being 0 or 1 to 6, m being 1 to 6

$R_{13}$ representing the radical

a monohydroxyalkyl radical or a polyhydroxyalkyl radical whose hydroxyls are optionally protected in methoxy or acetoxy form, an epoxidized lower alkyl radical or the radical

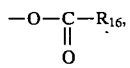

$R_{15}$ representing the radical $OR_{16}$ or the radical

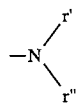

$R_{16}$ representing a hydrogen atom, a lower alkyl radical, an aryl radical or an aralkyl radical, $R_{14}$ representing a hydroxyl radical when m>2, a monohydroxyalkyl radical, a polyhydroxyalkyl radical, the radical

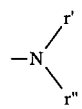

the radical

a mono- or polyhydroxylated alkenyl radical having 2 to 10 carbon atoms, or when $R_2$ and $R_3$ are not taken together, m may be 0 and/or $R_{14}$ may represent a hydrogen atom or a lower alkyl radical, $R_6$ and $R_7$ represent a hydrogen atom, a halogen atom, a lower alkyl radical or the radical —$OR_{16}$, $R_5$ and $R_6$ may, in addition, form a methylenedioxy ring when $R_6$ is in the 3-position of the benzene nucleus, and the salts of the compounds of formula (I) when $R_1$ or $R_{13}$ represent a carboxylic acid functional group or when $R_{14}$ represents an amine functional group and the chiral analogues of the said compounds of formula (I) and the geometric isomers of the said compounds when $R_2$ and $R_3$ are not taken together.

When the compounds according to the invention exist in the form of salts, when $R_1$ or $R_{13}$ represent a carboxylic functional group, in this case, these are salts of an alkali or alkaline-earth metal or alternatively of zinc or of an organic amine.

When $R_{14}$ represents an amine functional group, in this case, they are pharmaceutically or cosmetically acceptable salts formed by addition of an organic or inorganic acid, in particular hydrochloric, sulphuric, acetic, citric, fumaric, hemisuccinic, maleic and mandelic acid.

Lower alkyl radical is understood to mean a radical having 1 to 6 carbon atoms and preferably methyl, ethyl, isopropyl, butyl and tert-butyl radicals.

Lower alkoxy radical should be understood to mean radicals having 1 to 4 carbon atoms, especially methoxy, ethoxy, isopropoxy or butoxy radicals.

Cycloaliphatic radical should be understood to mean a mono- or polycyclic radical such as for example the 1-methylcyclohexyl or 1-adamantyl radical.

Monohydroxyalkyl radical should be understood to mean a radical having 1 to 6 carbon atoms, especially a hydroxymethyl, 2-hydroxyethyl, 2-hydroxypropyl, 3-hydroxypropyl, 4-hydroxybutyl, 5-hydroxypentyl or 6-hydroxyhexyl radical.

Polyhydroxyalkyl radical should be understood to mean a radical containing 3 to 6 carbon atoms and 2 to 5 hydroxyl groups such as 2,3-dihydroxypropyl, 2,3,4-trihydroxybutyl or 2,3,4,5-tetrahydroxypentyl radicals or the pentaerythritol residue.

Aryl radical should be understood to mean a phenyl radical optionally substituted by at least one halogen atom, a hydroxyl or a nitro functional group.

Aralkyl radical should be understood to mean the benzyl or phenethyl radical optionally substituted by at least one halogen atom, a hydroxyl or a nitro functional group.

When the radicals $R_6$ and $R_7$ represent a halogen atom, the latter is preferably a chlorine, bromine or fluorine atom.

Amino acid residue should be understood to mean a residue derived from lysine, glycine or aspartic acid.

A sugar residue should be understood to mean a residue derived for example from glucose, galactose or mannose.

Heterocycle is understood to mean preferably a piperidino, morpholino, pyrrolidino or piperazino radical, optionally substituted in the 4-position by a $C_1$-$C_6$ alkyl radical or a mono- or polyhydroxyalkyl radical as defined above.

Among the compounds of formula (I) above, the following may be especially mentioned:

1) 6-[3-(1-Adamantyl)-4-(3-aminopropyloxy)phenyl]-2-naphthoic acid hydrochloride;
2) Methyl 6-[3-(1-adamantyl)-4-(2,3-dihydroxypropyloxy)phenyl]-2-naphthoate;
3) 6-{3-(1-Adamantyl)-4-(2,3-dihydroxypropyloxy)phenyl]-2-naphthoic acid;
4) Benzyl 6-[3-(1-adamantyl)-4-methoxycarbonylmethyloxyphenyl]-2-naphthoate;
5) 6-[3-(1-Adamantyl)-4-methoxycarbonylmethyloxyphenyl]-2-naphthoic acid;
6) 6-[3-(1-Adamantyl)-4-carboxymethyloxyphenyl]-2-naphthoic acid;
7) Methyl 6-[3-(1-adamantyl)-4-(3-hydroxypropyloxy)phenyl]-2-naphthoate;
8) 6-[3-(1-Adamantyl)-4-(3-hydroxypropyloxy)phenyl]-2-naphthoic acid;
9) Methyl 6-[3-(1-adamantyl)-4-benzyloxycarbonylphenyl]-2-naphthoate;
10) Methyl 6-[3-(1-adamantyl)-4-carboxyphenyl]-2-naphthoate;
11) Methyl 6-[3-(1-adamantyl)-4-hydroxymethylphenyl]-2-naphthoate;
12) 6-[3-(1-Adamantyl)-4-hydroxymethylphenyl]-2-naphthoic acid;
13) 6-[3-(1-Adamantyl)-4-acetoxymethylphenyl]-2-naphthoic acid;
14) Methyl 6-[3-(1-adamantyl)-4-methoxycarbonylphenyl]-2-naphthoate;
15) 6-[3-(1-Adamantyl)-4-methoxycarbonylphenyl]-2-naphthoic acid;
16) 6-[3-(1-Adamantyl)-4-carboxyphenyl]-2-naphthoic acid;
17) 6-[3-(1-Adamantyl)-4-carboxamidophenyl]-2-naphthoic acid;
18) Benzyl 6-[3-(1-adamantyl)-4-methoxycarbonylethenylphenyl]-2-naphthoate;
19) 6-[3-(1-Adamantyl)-4-(methoxycarbonylethyl)phenyl]-2-naphthoic acid;
20) Benzyl 6-[3-(1-adamantyl)-4-(2,3-epoxypropyl)phenyl]-2-naphthoate;
21) 6-[3-(1-Adamantyl)-4-(2-hydroxypropyl)phenyl]-2-naphthoic acid;
22) 6-[3-(1-Adamantyl)-4-(3-methoxy-2-hydroxypropyl)phenyl]-2-naphthoic acid;
23) 4-[(E)-2-(3-(1-adamantyl)-4-methoxyphenyl)propenyl]benzoic acid;
24) Benzyl 4-[(E)-2-(3-(1-adamantyl)-4-methoxyphenyl)propenyl]benzoate;
25) 4-[(E)-2-(3-(1-adamantyl)-4-hydroxyphenyl)-1-propenyl] benzoic acid;
26) 6-[3-(1-Adamantyl)-4-methoxycarbonylphenyl]-2-naphthylcarboxamide;
27) Ethyl 4-[(E)-2-(3-(1-methylcyclohexyl)-4-hydroxyphenyl)propenyl]benzoate;
28) Ethyl 4-[(E)-2-(3-(1-methylcyclohexyl)-4-methoxyphenyl)propenyl]benzoate;
29) 4-[(E)-2-(3-(1-methylcyclohexyl)-4-methoxyphenyl)propenyl]benzoic acid;
30) Ethyl 4-[(Z)-2-(3-(1-methylcyclohexyl)-4-hydroxyphenyl)propenyl]benzoate;
31) Ethyl 4-[(Z)-2-(3-(1-methylcyclohexyl)-4-methoxyphenyl)propenyl]benzoate;
32) 4-[(Z)-2-(3-(1-methylcyclohexyl)-4-methoxyphenyl)propenyl]benzoic acid;
33) Ethyl 4-[(Z)-2-(3-tert-butyl-4-methoxyphenyl)propenyl]benzoate;
34) 4-[(Z)-2-(3-tert-butyl-4-methoxyphenyl)propenyl]benzoic acid;
35) 4-[(E)-2-(3-tert-butyl-4-hydroxyphenyl)propenyl]benzoic acid;
36) 4-[(E)-2-(3-(1-methylcyclohexyl)-4-hydroxyphenyl)ethenyl]benzoic acid;
37) Ethyl 4-[(E)-2-(3-(1-methylcyclohexyl)-4-(6-tertbutoxycarbonylpentyloxy)phenyl)ethenyl]benzoate;
38) Ethyl 4-[(E)-2-(3-(1-methylcyclohexyl)-4-(6-carboxypentyloxy)phenyl)ethenyl]benzoate;
39) 4-[(E)-2-(3-(1-adamantyl)-4-hydroxyphenyl)ethenyl] benzoic acid;
40) Benzyl 6-[3-(1-adamantyl)-4-(1,2-dihydroxyethyl)phenyl]-2-naphthoate;

41) 6-[3-(1-Adamantyl)-4-(1,2-dihydroxyethyl)phenyl]-2-naphthoic acid;
42) Benzyl 6-[3-(1-adamantyl)-4-(3-hydroxypropyl)phenyl]-2-naphthoate;
43) 6-[3-(1-Adamantyl)-4-(3-hydroxypropyl)phenyl]-2-naphthoic acid;
44) Benzyl 6-[3-(1-adamantyl)-4-(3-acetoxypropyl)phenyl]-2-naphthoate;
45) 6-[3-(1-Adamantyl)-4-(3-acetoxypropyl)phenyl]-2-naphthoic acid;
46) Benzyl 6-[3-(1-adamantyl)-4-(2,3-dihydroxypropyl)phenyl]-2-naphthoate;
47) 6-[3-(1-Adamantyl)-4-(2,3-dihydroxypropyl)phenyl]-2-naphthoic acid;
48) N-methoxycarbonylmethyl-4-(6-benzyloxycarbonylnaphthyl)-2-(1-adamantyl)phenylcarboxamide;
49) N-methoxycarbonylmethyl-4-(6-carboxynaphthyl)-2-(1-adamantyl)phenylcarboxamide;
50) 6-[3-(1-Adamantyl)-4-(N,N-dimethylcarbamoyl)phenyl]-2-naphthoic acid;
51) Benzyl 6-[3-(1-adamantyl)-4-(2(R),3-dihydroxypropyloxy)phenyl]-2-naphthoate;
52) 6-[3-(1-Adamantyl)-4-(2(R),3-dihydroxypropyloxy)phenyl]-2-naphthoic acid;
53) 6-[3-(1-Adamantyl)-4,5-methylenedioxyphenyl]-2-naphthoic acid;
54) N-ethyl 6-[3-(1-adamantyl)-4-methoxycarbonylphenyl]-2-naphthylcarboxamide;
55) N,N-morpholyl 6-[3-(1-adamantyl)-4-methoxycarbonylphenyl]-2-naphthylcarboxamide;
56) 4-[(E)-2-(3-tert-butyl-4-methoxyphenyl)propenyl]phenylcarbinol; and
57) 4-(E)-2-(3-tert-butyl-4-methoxyphenyl)propenyl]benzylacetate.

The subject of the present invention is also the process for preparing the compounds of formula (I).

The compounds of formula (I) for which $R_2$ and $R_3$, taken together, form with the benzene nucleus a naphthalene ring are obtained by a coupling reaction between a halogenated derivative (1) and a halogenated derivative of formula (2):

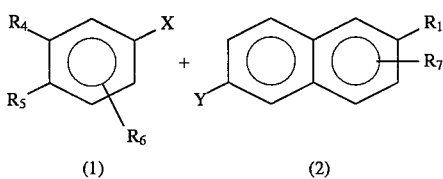

(1)     (2)

X and Y representing a chlorine, bromine or iodine atom.

In a first stage, the halide (1) is converted to a lithium, magnesium or zinc compound and is then coupled to the derivative (2) in the presence of a nickel or palladium catalyst, according to the biaryl coupling conditions described by E. Negishi et al., J. Org. Chem. (1977) 42, 1821.

The compounds of formula (I) for which $R_2$ and $R_3$ are not taken together can be obtained by the following reaction scheme using a Wittig or Horner-Emmons reaction (see Table I).

In these olefination reactions, the geometric isomer of E configuration can also be obtained by conversion, under irradiation under UV light, of the isomer of geometric Z configuration.

In these formulae, $R_1$, $R_4$, $R_6$ and $R_7$ have the same meanings as those given above for the general formula or are derivatives thereof which are conveniently protected in order to be compatible with the coupling conditions. In particular, the substituent $R_5$ is a phenol protected in the form of tert-butyldimethylsilyloxy or an alkoxy radical.

The derivative obtained is then converted to phenol by deprotection at the level of the substituent $R_5$ of the TBDMS or alkoxy group and is then treated according to one of the two routes mentioned below:

treatment of the phenol thus obtained by a metal hydride which is reacted with a halide, conversion of the phenol thus obtained to triflate and then nucleophilic substitution in the presence of a palladium catalyst (see Table II) according to the general conditions described by:

S. Cacchi et al., Tetrahedron Letter, 1986, 27, 3931–3934
W. J. Scott et al., J. Org. Chem., 1985, 50, 2302–2308

In the case where $R_2$ and $R_3$ are not taken together, it is preferable to carry out this nucleophilic substitution reaction before the olefination reaction (Wittig or Horner-Emmons) described in Table I.

The subject of the present invention is also, as intermediate product in the synthesis of the compounds according to the invention, the following compounds:

6-[3-(1-Adamantyl)-4-(3-aminopropyloxy)phenyl]-2-naphthoic acid,
3-(1-Adamantyl)-4-(2,2-dimethyl-1,3-dioxolane-4-methyloxy)bromobenzene, and
Methyl 6-[3-(1-adamantyl)-4-(2,2-dimethyl-1,3-dioxolane-4-methyloxy)phenyl]-2-naphthoate.

The subject of the present invention is also, as medicinal product, the compounds of formula (I) as defined above.

The compounds of the invention have good stability to light and to oxygen.

These compounds exhibit an activity in the test of differentiation of mouse embryonic teratocarcinoma cells (F9) (Cancer Research 43, p.5268, 1983) and/or in the test of inhibition of ornithine decarboxylase after induction by TPA in mice (Cancer Research 38, p.793–801, 1978). These tests show the activities of the compounds in the cellular differentiation and proliferation domains respectively.

The compounds according to the invention are particularly suitable in the following treatment domains:

1) For treating dermatological conditions linked to a keratinization disorder affecting differentiation and proliferation especially for treating acne vulgaris, comedo type acnes, polymorphic acnes, nodulokystic acnes, acne conglobata, senile acnes, secondary acnes such as solar acne, acne medicamentosa, occupational acne.

2) For treating other types of keratinization disorder, especially ichthyosis, ichthyosiform states, Darier's disease, keratosis palmaris et plantaris, leukoplakias and leukoplakia-like states, skin or mucous lichen, 3) For treating other dermatological conditions linked to a keratinization disorder with an inflammatory and/or immunoallergic component and, especially, all the forms of psoriasis whether cutaneous, mucous or ungual, and even arthropathic psoriasis, or even skin atopy, such as eczema, or respiratory atopy or gingival hypertrophy; the compounds may also be used in certain inflammatory conditions not exhibiting keratinization disorder.

4) For treating all dermal or epidermal proliferations whether benign or malignant, whether they are of viral origin such as verruca vulgaris, verruca plana and epidermodysplasia verruciformis, florid oral papillomatoses and proliferations which can also be induced by ultraviolet radiation especially in the case of baso- and spinocellular epithelioma.

5) For treating other dermatological disorders such as bullous dermatoses and collagen diseases.

6) For treating certain ophthalmological diseases, especially corneopathies.

7) For repairing and controlling skin aging, whether photoinduced or chronological or to reduce actinic pigmentations and keratoses.

8) For preventing or healing the stigmas of epidermal and/or dermal atrophy induced by local or systemic corticosteroids, or any other form of skin atrophy.

9) For preventing or treating cicatrization disorders, for preventing and repairing vibices.

10) For controlling disorders of the sebaceous function such as acne hyperseborrhoea or ordinary seborrhoea.

11) In the treatment of cancer or precancer situations, in particular in the skin.

12) In the treatment of inflammatory conditions such as arthritis.

The subject of the present invention is also medicinal compositions containing at least one compound of formula (I) as defined above, or one of its salts.

The subject of the present invention is therefore also a new medicinal composition intended especially for the treatment of the abovementioned conditions, characterized by the fact that it comprises, in a pharmaceutically acceptable carrier, at least one compound of formula (I) and/or one of its salts.

The compounds according to the invention are generally administered at a daily dose of about 0.01 mg/kg to 100 mg/kg of body weight in 1 to 3 doses.

The administration may be performed enterally, parenterally, topically or ocularly. For enteral administration, the medicinal products may be provided in the form of tablets, hard gelatin capsules, sugar-coated tablets, syrups, suspensions, solutions, powders, granules, emulsions, or lipid or polymeric microspheres or nanospheres or vesicules which permit a controlled release. For parenteral administration, the compositions may be provided in the form of solutions or suspensions for perfusion or for injection.

For topical administration, the pharmaceutical compositions based on compounds according to the invention are intended for the treatment of the skin and the mucous membranes and are provided in the form of ointments, creams, milks, pommades, powders, impregnated pads, solutions, gels, sprays, lotions or suspensions. They may also be provided in the form of lipid or polymeric microspheres or nanospheres or vesicules or polymeric patches or hydrogels which permit a controlled release.

These compositions for topical administration may be provided either in anhydrous form, or in aqueous form according to the clinical indication.

For ocular administration, they are mainly collyria.

These compositions contain at least one compound of formula (I) as defined above or one of its salts, at a concentration preferably of between 0.001 and 5% relative to the total weight of the composition.

The compounds of formula (I), according to the invention, also find application in the cosmetic field, in particular in body and hair care and especially for the treatment of skins with a tendency to develop acne, for hair regrowth, for combatting hair loss, for controlling the greasy appearance of the skin or the hair, for protection against the harmful effects of the sun and in the treatment of physiologically dry skins.

The present invention therefore also relates to a cosmetic composition containing, in a cosmetically acceptable carrier, at least one compound of formula (I) or one of its salts, this composition being provided especially in the form of a cream, a milk, a lotion, a gel, or lipid or polymeric microspheres or nanospheres or vesicules, a soap or a shampoo.

The concentration of compound of formula (I) in the cosmetic compositions is preferably between 0.001 and 3% by weight.

The medicinal and cosmetic compositions according to the invention may contain inert or even pharmacodynamically or cosmetically active additives or combinations of these additives and especially: wetting agents, depigmenting agents such as hydroquinone, azelaic acid, caffeic acid, kojic acid, emollient agents, moisturizing agents such as glycerol, PEG 400, thiamorpholinone and its derivatives or urea; antiseborrhoeic or antiacne agents such as S-carboxymethylcysteine, S-benzylcysteamine, their salts and their derivatives, tioxolone or benzoyl peroxide; antibiotics such as erythromycin and its esters, neomycin, clindamycin and its esters, tetracyclines; anti-fungal agents such as ketoconazole or 4,5-polymethylene- 3-isothiazolinones; agents which promote hair regrowth, such as "Minoxidil" (2,4-diamino-6-piperidinopyrimidine 3-oxide) and its derivatives, Diazoxide (7-chloro-3-methyl-1,2,4-benzothiadiazine 1,1-dioxide) and Phenytoin (5,5-diphenyl-2,4-imidazolidinedione); steroidal and non-steroidal anti-inflammatory agents; carotenoids and, especially β-carotene; antipsoriatic agents such as anthralin and its derivatives and 5,8,11,14-eicosatetraynoic and 5,8,11-eicosatriynoic acids, their esters and their amides or anti-irritant agents such as derivatives of α-hydroxy acids and more particularly the derivatives of mandelic acid.

The compositions according to the invention may also contain flavour enhancing agents, preserving agents such as para-hydroxybenzoic acid esters, stabilizing agents, moisture regulating agents, pH regulating agents, osmotic pressure modifying agents, emulsifying agents, UV-A and UV-B screening agents, antioxidants such as α-tocopherol, butylated hydroxyanisole or butylated hydroxytoluene.

Several examples of preparation of the active compounds of formula (I) according to the invention as well as examples of compositions containing them will now be given as illustration and with no limitation being implied.

EXAMPLE 1

6-[3-(1-Adamantyl)-4-(3-aminopropyloxy)phenyl]-2-naphthoic acid hydrochloride.

a) Methyl 6-[3-(1-adamantyl)-4-(N-triphenylmethyl-3-aminopropyloxy)phenyl]-2-naphthoate 360 mg (12 mmol) of sodium hydride (80% in oil) and 50 ml of DMF are introduced into a three-necked round-bottomed flask. A solution of 4.1 g (10 mmol) of methyl 6-[3-(1-adamantyl)-4-hydroxyphenyl]-2-naphthoate in 75 ml of DMF are added dropwise, under a nitrogen stream, and the mixture is stirred until the evolution of gas ceases. A solution of 42 g (11 mmol) of N-triphenylmethyl- 3-bromopropylamine in 50 ml of DMF is then introduced dropwise and the mixture is stirred at room temperature for 8 h. The reaction medium is poured into water, extracted with ethyl ether, the organic phase separated after settling has taken place, washed with water, dried over magnesium sulphate and evaporated. The residue obtained is purified by silica chromatography, eluted with a dichloromethane and hexane mixture (40–60). After evaporation of the solvents, 4.7 g (66%) of the expected product are recovered, which product melts at 168°–9° C.

b) 6-[3-(1-Adamantyl-4-(N-triphenylmethyl-3-aminopropyloxy)phenyl]-2-naphthoic acid 4.5 g (6.3 mmol) of the preceding product and 100 ml of 2N methanolic sodium hydroxide are introduced into a round-bottomed flask. The mixture is refluxed for 4 hours, evaporated to dryness, the residue taken up in water and acidified to pH=1 with concentrated hydrochloric acid. The solid which precipitates is filtered, and is washed with water and then with 20 ml of acetone. After drying in the presence of phosphorus pentoxide, 4.1 g (93%) of the expected acid, with a melting point of 243°–4° C., are recovered.

c) 6-[3-(1-Adamantyl)-4-(3-aminopropyloxy)phenyl]-2-naphthoic acid 2.8 g (4 mmol) of the preceding acid, 200 ml of acetic acid and 100 ml of 6N hydrochloric acid are introduced into a round-bottomed flask. The mixture is refluxed for 12 h, the reaction mixture is cooled and the solid is filtered. The solid obtained is introduced into 30 ml of water and the pH is adjusted to 5, the solid is filtered, it is washed with water and then with 100 ml of acetone, and dried in the presence of phosphorus pentoxide. 1.6 g (89%) of the expected acid is recovered which melts with decomposition at 294°–7° C.

d) 6-[3-(1-Adamantyl)-4-(3-aminopropyloxy)phenyl]-2-naphthoic acid hydrochloride.

455 mg (1 mmol) of the preceding product and 100 ml of methanol are introduced into a round-bottomed flask. A solution of hydrochloric acid in isopropyl alcohol (2N) is added dropwise up to pH=1 and the reaction medium is evaporated to dryness. The residue is triturated in 20 ml of acetone, the solid obtained is filtered, washed with 50 ml of ethyl ether and dried under vacuum at 80° C. 430 mg (88%) of the expected hydrochloride are recovered, which hydrochloride melts at 303°–6 ° C. with decomposition.

EXAMPLE 2

Methyl 6-[3-(1-adamantyl)-4-(2,3-dihydroxypropyloxy)phenyl]-2-naphthoate a) 3-(1-Adamantyl)-4-(2,2-dimethyl-1,3-dioxolane-4-methyloxy)bromobenzene 11.2 g (39 mmol) of 3-tosyloxy-1,2-propanediolacetonide are added dropwise, with stirring, to a solution of 10 g (32.5 mmol) of 3-(1-adamantyl)-4-bromophenol in 140 ml of dimethylformamide containing 4.95 g (35.8 mmol) of potassium carbonate. The reaction medium is left at 100° C. overnight, then poured into ice cold water and extracted with ether. After washing the organic phase, drying and evaporation, the residue is chromatographed on silica in the dichloromethane/hexane mixture (50/50) to give 7.5 g (55%) of the expected product which melts at 90.6° C.

b) Methyl 6-[3-(1-adamantyl)-4-(2,2-dimethyl-1,3-dioxolane- 4-methyloxy)phenyl]-2-naphthoate.

7.4 g (17.6 mmol) of 3-(1-adamantyl)-4-(2,2-dimethyl-1,3-dioxolane-4-methyloxy)bromobenzene in 50 ml of tetrahydrofuran and 300 ml of dibromoethane are added to a three-necked round-bottomed flask, under nitrogen, containing 962 mg of magnesium in 100 ml of THF. The mixture is refluxed for 1 h 30 min, it is allowed to cool and 5.09 g (37.6 mmol) of zinc chloride are added, the mixture is stirred for 1 h and 9.97 g (37.6 mmol) of methyl 6-bromo-2-naphthoate in 50 ml of THF, then 300 mg of $NiCl_2$/DPPE complex are added successively. The mixture is stirred for 8 h at room temperature., poured into a saturated aqueous ammonium chloride solution, extracted with ether and the organic phase is washed and evaporated. The residue is chromatographed on silica in the hexane/dichloromethane mixture (70/30) to give 8.3 g (89%) of the expected derivative which melts at 116°–118° C.

c) Methyl 6-[3-(1-adamantyl)-4-(2,3-dihydroxypropyloxy)phenyl]-2-naphthoate.

4.8 g (9.15mmol) of the ester (2b) are suspended in 90 ml of a 40% aqueous formic acid solution. The mixture is heated at 100° C. for 48 h. The reaction medium is poured into water and is extracted with ethyl acetate. After washing the organic phase with water, drying and evaporation, the residue is chromatographed on silica in the $CH_2Cl_2$/THF eluent (90/10) to give 3.2 g (72%) of the expected derivative which melts at 209.6° C.

EXAMPLE 3

6-[3-(1-Adamantyl)-4-(2,3-dihydroxypropyloxy)phenyl]-2-naphthoic acid.

3 g of the ester obtained in Example 2(c) are suspended in the presence of 1.5 g of sodium hydroxide in 60 ml of methanol. The reaction medium is refluxed for 24 H. After evaporation of the methanol, the residue is taken up in water, acidified to pH=1 (concentrated HCl) and extracted with ethyl acetate. The organic phase is washed, dried and evaporated to give 2.67 g (92%) after recrystalization from ethyl acetate, of the expected derivative which melts at 277.8° C.

EXAMPLE 4

Benzyl 6-[3-(1-adamantyl)-4-methoxycarbonylmethyloxyphenyl]-2-naphthoate.

a) Benzyl 6-[3-(1-adamantyl)-4-hydroxyphenyl]-2-naphthoate.

39.85 g (0.1 mol) of 6-[3-(1-adamantyl)-4-hydroxyphenyl]-2-naphthoic acid in 400 ml of DMF are placed in a three-necked round-bottomed flask under nitrogen and 3.2 g of 80% NaH in oil are added in portions. The mixture is left stirring at room temperature for 1 h, then 13.2 ml (0.11 mol) of benzyl bromide are added dropwise and the mixture is left stirring at room temperature overnight. The reaction medium is poured into ice cold water and it is extracted with 1.8 l of ether. The organic phase is washed with water, dried and evaporated. The residue is chromatographed on silica in the dichloromethane/hexane mixture (70/30) to give 42.2 g (79%) of the expected derivative which melts at 185°–186° C.

b) Benzyl 6-[3-(1-adamantyl)-4-methoxycarbonylmethyloxyphenyl]-2-naphthoate.

136 mg of 80% sodium hydride in oil are added to a solution of 8 g (16mmol) of benzyl 6-[3-(1-adamantyl)-4-hydroxyphenyl]-2-naphthoate in 100 ml of DMF. The mixture is left stirring for 1 h and 1.6 ml (16.4 mmol) of methyl bromoacetate are added. The reaction mixture is left stirring overnight, and it is then poured into ice cold water and acidified to pH 2 with concentrated HCl. The solid is filtered and recrystallized from ether. 8.52 g (95%) of the expected derivative are recovered, which derivative melts at 183° C.

EXAMPLE 5

6-[3-(1-Adamantyl)-4-methoxycarbonylmethyloxyphenyl]-2-naphthoic acid.

4.24 g (7.58 mmol) of the diester obtained in Example 4 in solution in the dioxane/acetic acid mixture (99/1) are treated with 800 mg of Pd-C (10%) at a pressure of 7 bar of hydrogen at 40° C. for 6 h. The reaction medium is then filtered on celite, evaporated, washed with water and recrystallized from the acetate/tetrahydrofuran mixture. 2.94 g (82%) of a solid are isolated, which solid melts at 283°–285° C.

EXAMPLE 6

6-[3-(1-Adamantyl)-4-carboxymethyloxyphenyl]- 2-naphthoic acid.

1 g (2.1 mmol) of the monoester obtained in Example 5 is treated with 0.58 g of KOH in 50 ml of n-butanol. The mixture is heated at 100° C. for 1 h 30 min, then the butanol is evaporated, the solid is taken up in 50 ml of water, acidified to pH=1 with concentrated HCl and filtered. After drying, washing with ether and recrystallization from THF, 720 mg of the expected product are isolated, which product melts at 332°–335° C.

EXAMPLE 7

Methyl 6-[3-(1-adamantyl)-4-(3-hydroxypropyloxy)phenyl]-2-naphthoate;

77 mg (2.55 retool) of 80% sodium hydride in oil are added to 1 g (2.42 mmol) of methyl 6-[3-(1-adamantyl)-4-hydroxyphenyl]-2-naphthoate in solution in 10 ml of DMF. After 1 h 30 min of stirring, 230 ml (2.42 mmol) of bromopropanol are added to this reaction medium which is left stirring for 12 hours at room temperature, under nitrogen. The reaction medium is poured into water, acidified to pH=1 with concentrated HCl and extracted with ethyl acetate. The organic phase is washed with water, dried over magnesium sulphate, filtered and evaporated. The residue is chromatographed on silica in dichloromethane, and crystallized from the dichloromethane/hexane mixture to give 600 mg (53%) of the expected derivative which melts at 201.9° C.

EXAMPLE 8

6-[3-(1-Adamantyl)-4-(3-hydroxypropyloxy)phenyl]-2-naphthoic acid.

0.57 g (1.21 mmol) of the ester obtained in Example 7 in suspension in 30 ml of n-butanol is treated with 400 mg of potassium hydroxide. The reaction mixture is heated for 3 h at 100° C., then evaporated to dryness, and is taken up in 50 ml of water and washed with ether. The aqueous phase is acidified to pH=1 with concentrated HCl and extracted with 600 ml of ether. The organic phase is washed with water, dried over magnesium sulphate, filtered and evaporated to give 0.49 g (90%) of the expected acid which melts at 277°–279° C.

EXAMPLE 9

Methyl 6-[3-(1-adamantyl)-4-benzyloxycarbonylphenyl]-2-naphthoate.
a) Methyl 6-[3-(1-adamantyl)-4-trifluoromethylsulphonyloxyphenyl]-2-naphthoate.

59 mg of dimethylaminopyridine and 12 ml of pyridine are added to 19.8 g (48 mmol) of methyl 6-[3-(1-adamantyl)- 4-hydroxyphenyl]-2-naphthoate in 200 ml of $CH_2Cl_2$. 9.7 ml (0.057 mmol) of trifluoromethanesulphonic anhydride in 10 ml of $CH_2Cl_2$ are added dropwise to this solution, under nitrogen, cooled to −70° C. The temperature is allowed to rise to room temperature overnight, with stirring. The reaction medium is poured into ice cold water and is extracted with 1 l of ether. The organic phase is washed with an acid solution (1N HCL), it is then rinsed with water, dried over magnesium sulphate, filtered and evaporated. After chromatography on silica in the dichloromethane/hexane mixture (40/60) and recrystallization from the same solvent, 23.5 g (90%) of the expected product are obtained, which product melts at 185.5° C.
b) Methyl 6-[3-(1-adamantyl)-4-benzyloxycarbonylphenyl]-2-naphthoate.

13.11 g (0.024 mmol) of the triflate obtained above in 100 ml of DMF, 6.70 ml (0.048 mol) of triethylamine, 270 mg (5 mol %) of palladium acetate, 1.33 g (2.4 mmol) of diphenylphosphinoferrocene (DPPF) and 25 ml of benzyl alcohol are placed in an autoclave reactor. The reaction mixture is heated at 70° C., under 3 bar of carbon monoxide, for 6h. The reaction medium is then diluted with saturated sodium chloride, extracted with 1 l of ether, the organic phase washed with, 1N HCl, then with water, dried over magnesium sulphate and evaporated. The product is isolated after chromatography on silica in the $CH_2Cl_2$/hexane mixture (40/60). 9.15 g (72%) of the expected derivative are obtained, which derivative melts at 170° C.

EXAMPLE 10

Methyl 6-[3-(1-adamantyl)-4-carboxyphenyl]-2-naphthoate.

9.02 g (17 mmol) of the diester obtained in Example 9(b) in 90 ml of dioxane and 5 ml of acetic acid are placed in an autoclave reactor. 900 mg of Pd-C (10%) are then added and the mixture is treated at 70° C., with stirring, with a hydrogen pressure of 7 bar for 4 h. After removal of the catalyst, the filtrate is evaporated and the residue is washed with water and with hexane to give 6.81 g (91%) of the expected derivative which melts at 239°–240° C.

EXAMPLE 11

Methyl 6-[3-(1-adamantyl)-4-hydroxymethylphenyl]-2-naphthoate.

6.2 g (0.014 mol) of the acid obtained in Example 10 are dissolved in 30 ml of THF and treated with 49 ml of $BH_3$ (1M) in THF. The reaction medium is refluxed for 12 h, it is then evaporated, taken up in 900 ml of water and treated with 35 ml of 1N HCl. It is extracted with 800 ml of ethyl acetate, and the organic phase is washed with water and evaporated. The residue is chromatographed on silica in dichloromethane to give 4.45 g (75%) of the expected derivative which melts at 212° C.

EXAMPLE 12

6-[3-(1-Adamantyl)-4-hydroxymethylphenyl]-2-naphthoic acid.

4.40 g (103 mmol) of the ester obtained in Example 11 in 50 ml of methanol are treated with 4 g of sodium hydroxide, with stirring, for 1 h 30 min. After the same treatment as in Example 8 and recrystallization from the ethanol/water mixture, 3 g (96%) of the expected product are isolated, which product melts at 267°–270° C.

EXAMPLE 13

6-[3-(1-Adamantyl)-4-acetoxymethylphenyl]-2-naphthoic acid.

2.42 g (5.87 mmol) of the alcohol obtained in Example 12 in 12 ml of pyridine are treated with 0.63 ml of acetyl chloride for 30 min. The reaction medium is poured into ice cold water, and extracted with ethyl acetate. The organic phase is washed with water, dried over magnesium sulphate and evaporated to give, after recrystallization from the ethyl acetate/hexane mixture, 1.67 g (63%) of a product which melts at 251° C.

EXAMPLE 14

Methyl 6-[3-(1-adamantyl)-4-methoxycarbonylphenyl]-2-naphthoate.

3 g (5.5 mmol) of the triflate (9a) obtained in Example 9 in 30 ml of DMF and 1.54 ml of triethylamine and 8 ml of methanol are treated with 63.8 mg (5 mol %) of palladium acetate and 304.7 mg (10 mol %) of diphenylphosphinoferrocene and they are then subjected to a carbon monoxide pressure of 1 bar for 30 min at 70° C. The reaction medium is then poured into a saturated sodium chloride solution and extracted with ether. The organic phase is washed with 1N HCl, then with water, dried and evaporated. The residue is chromatographed on silica to give 1.9 g (75%) of the expected derivative which melts at 181°–182° C.

EXAMPLE 15

6-[3-(1-Adamantyl)-4-methoxycarbonylphenyl]- 2-naphthoic acid.

0.34 g of sodium hydroxide is added to 1.92 g (4.22 mmol) of the diester obtained in Example 14 in 25 ml of methanol and the mixture is kept under reflux for 24 hours. After the same treatment as in Example 8 and recrystallization from the isopropyl ether-ethyl acetate mixture, 1.7 g (91%) of the expected derivative are isolated, which derivative melts at 272°–273° C.

EXAMPLE 16

6-[3-(1-Adamantyl)-4-carboxyphenyl]-2-naphthoic acid.

2 g of potassium hydroxide are added to a solution of 1.20 g (2.72 mmol) of the diester obtained in Example 15 in 50 ml of n-butanol and the mixture is heated at 110° C. for 24 hours. After the same treatment as in Example 8, and recrystallization from the ethyl acetate-THF mixture, 605 mg (52%) of the expected derivative are isolated, which derivative melts at 333°–335° C.

EXAMPLE 17

6-[3-(1-Adamantyl)-4-carboxamidophenyl]-2-naphthoic acid.

a) Methyl 6-[3-(1-adamantyl)-4-carboxamidophenyl]-2-naphthoate.

15 ml of thionyl chloride are added to 1.91 g (4.34 mmol) of the acid obtained in Example 10 and the mixture is refluxed for 40 min. It is evaporated to dryness and the solid is taken up in 20 ml of dichloromethane and ammonia gas is bubbled through at 0° C. The reaction medium is allowed to return to room temperature overnight, then 800 ml of dichloromethane are added, washed with water, dried over magnesium sulphate and evaporated. After chromatography on silica in a hexane/ether (50/50) to ether (100%) elution gradient, the product is isolated and 0.94 g (49%) of the expected product is obtained which melts at 285° C.

b) 6-[3-(1-Adamantyl)-4-carboxamidophenyl]-2-naphthoic acid.

Following the procedure described in Example 15, 935 mg (2.1 mmol) of the preceding ester are saponified. The solid obtained is recrystallized from absolute ethanol. 450 mg (50%) of the expected derivative are obtained, which derivative melts at 322°–325° C.

EXAMPLE 18

Benzyl 6-[3-(1-adamantyl)-4-methoxycarbonylethenylphenyl]-2-naphthoate.

a) Benzyl 6-[3-(1-adamantyl)-4-trifluoromethylsulphonyloxyphenyl]-2-naphthoate.

59 mg of dimethylaminopyridine and 12 ml of pyridine are added to a solution of 23.5 g (48 mmol) of the phenol obtained in Example 4(a) in 150 ml of $CH_2Cl_2$, then this solution is placed at −70° C. and 9.70 ml (57.7 mmol) of trifluoromethanesulphonic anhydride in 10 ml of $CH_2Cl_2$ are added. The reaction medium is allowed to return to room temperature overnight, with stirring, then it is poured into ice cold water and extracted with 1 l of ether. The organic phase is washed with water, dried and evaporated. The residue is chromatographed on silica in the $CH_2Cl_2$/hexane mixture (40/60). After recrystallization from the dichloromethane/hexane mixture, 25.86 g (87%) of the expected derivative are isolated, which derivative melts at 132° C.

b) Benzyl 6-[ 3-(1-adamantyl)-4-(methoxycarbonylethenyl)phenyl]- 2-naphthoate.

6.7 ml (74.3mmol) of methyl acrylate, 15.5 ml of triethylamine (0.11 mmol) and 521 mg of $Pd(PPh_3)_2Cl_2$ are added to 11.53 g (18.58 mmol) of the compound obtained above in 100 ml of DMF. The mixture is heated at 90° C. for 5 days. The reaction medium is poured into ice cold water and is extracted with 1.2 l of ethyl acetate. The organic phase is washed, dried and evaporated to give, after chromatography on silica in the $CH_2Cl_2$/hexane mixture (40/60), 6.2 g (62%) of the expected derivative which melts at 159° C.

EXAMPLE 19

6-[3-(1-Adamantyl)-4-(methoxycarbonylethyl)phenyl]-2-naphthoic acid;

334 mg of Pd-C (10%) are added to a solution of 2.23 g (4 mmol) of the diester obtained in Example 18(b) in 50 ml of dioxane and 1 ml of acetic acid and the reaction mixture is stirred under a hydrogen pressure of 7 bar at 70° C. for 5 hours. The reaction medium is filtered on celite and evaporated. The filtrate is washed with water and dried to give, after recrystallization from ethyl acetate, 1.65 g (82%) of the expected derivative which melts at 259° C.

EXAMPLE 20

Benzyl 6-[3-(1-adamantyl)-4-(2,3-epoxypropyl)phenyl]-2-naphthoate.

a) Benzyl 6-[3-(1-adamantyl)-4-(2-propenyl)phenyl]-2-naphthoate.

6.4 ml (0.02 mol) of allyltributyltin and 1.70 g of lithium chloride are added to a solution of 1.24 g (0.02 mol) of the compound obtained in Example 18(a) in 60 ml of DMF and the mixture is left stirring under an inert atmosphere at room temperature for 30 min. 280 mg (0.4 mmol) of $PdCl_2(P(C_6H_5)_3)_2$ are then added and the mixture is gradually heated up to 100° C. for 40 min. The reaction medium is poured into ice cold water and extracted with 1 l of ether. The organic phase is washed with water, dried and evaporated. The residue is chromatographed on silica in the hexane/ether mixture (95/5) to give 11.6 g (95%) of the expected derivative which melts at 115° C.

b) Benzyl 6-[3-(1-adamantyl)-4-(2,3-epoxypropyl)phenyl]-2-naphthoate.

2.56 g (5 mmol) of the derivative obtained above, dissolved in 25 ml of $CH_2Cl_2$ are treated with 1.52 g of meta-chloroperbenzoic acid at 0° C. The medium is allowed to return to room temperature over 12 h, with stirring. The reaction medium is diluted with dichloromethane and washed with sodium hydrogen sulphite and then with sodium bicarbonate. The organic phase is dried and evaporated. The residue obtained is chromatographed on silica in the $CH_2Cl_2$/hexane mixture (60/40) to give 1.91 g (72%) of the expected derivative which melts at 118°–120° C.

EXAMPLE 21

6-[3-(1-Adamantyl)-4-(2-hydroxypropyl)phenyl]-2-naphthoic acid.

1.40 g (2.65 mmol) of the derivative obtained in Example 20(b) are dissolved in 50 ml of dioxane and 1 ml of acetic acid and are hydrogenated in the presence of 280 mg of Pd-C (10%) at 70° C., at a pressure of 7 bar, for 6 h. After filtration of the palladium and evaporation, the residue is chromatographed in the ether/hexane mixture (80/20) to give, after recrystallization from hexane, 523 mg (45%) of the expected product which melts at 282° C.

EXAMPLE 22

6-[3-(1-Adamantyl)-4-(3-methoxy-2-hydroxypropyl)phenyl]-2-naphthoic acid.

1 g (1.89 mmol) of the ester obtained in Example 20(b) in 100 ml of the methanol/THF mixture (1/1) are treated with 230 mg of sodium hydroxide and are left stirring overnight at room temperature and then for 3 h under reflux. After an identical treatment to that performed in Example 12 and recrystallization from the ethyl acetate/hexane mixture, 0.65 g (78%) of the expected derivative is obtained which melts at 240°–242° C.

EXAMPLE 23

4-[(E)-2-(3-(1-adamantyl)-4-methoxyphenyl)propenyl]benzoic acid.

a) 3-(1-Adamantyl)-4-methoxyphenylethanone 15.75 g (0,055 mol) of 3-(1-adamantyl)-4-methoxyphenylbenzoic acid in solution in 150 ml of toluene are treated with 7.3 ml of thionyl chloride and are heated at 100° C. for 3 h 30 min. The reaction medium is evaporated to dryness and then 30 ml of hexamethylphosphoramide, 8 ml (0.0575 mol) of tetramethyltin and 22 mg of PhCH$_2$Pd(PPh$_3$)$_2$Cl are added to this evaporation residue under nitrogen. The reaction medium is heated at 65° C. for 30 min and it is then left, with stirring, at room temperature overnight. The reaction medium is poured into water and extracted with ether. After chromatography on silica in the dichloromethane/hexane eluent (60/40), 10.47 g (71%) of the expected derivative are isolated, which derivative melts at 138°–140° C.

b) 4-[(E)-2-(3-(1-adamantyl)-4-methoxyphenyl)propenyl] benzoic acid.

0.90 g (0.03 mol) of 80% sodium hydride in oil is placed in a 250 ml three-necked round-bottomed flask, under nitrogen, and 8.58 g (0.03 mol) of diethyl 4-methoxycarbonylbenzylphosphonate in 15 ml of dimethoxyethane are added dropwise. 8.53 g (0.03 mol) of the derivative obtained in (a) above are then added and the mixture is heated for 10 h at 80° C. then at room temperature for 65 hours. The reaction medium is then poured into water, extracted with 1 l of ethyl acetate, the aqueous phase rinsed until the pH is neutral and evaporated. After chromatography on silica in the hexane/ethyl acetate mixture (95/5), 3 g of methyl 4-[(Z)-2-(3-(1-adamantyl)- 4-methoxyphenyl)propenyl]benzoate and 0.45 g of methyl 4-[(E)-2-(3-(1-adamantyl)-4-methoxyphenylpropenyl]benzoate are isolated.

0.45 g (1.1 mol) of the methyl ester of (E) configuration obtained above is treated with 0.2 g of sodium hydroxide in 5 ml of methanol and refluxed for 3 h 30 min. After the same treatment as in Example 1(b) and recrystallization from a THF-ethanol mixture, 0.2 g (52%) of 4-[ (E)-2-(3-(1-adamantyl)-4-methoxyphenyl)propenyl]benzoic acid is isolated which melts at 307°–308° C.

c) 4-[(Z)-2-(3-(1-adamantyl)-4-methoxyphenylpropenyl] benzoic acid.

3 g (7.2 mol) of methyl 4-[(Z)-2-(3-(1-adamantyl)-4-methoxyphenyl)propenyl]benzoate are treated with 4 g of sodium hydroxide in 50 ml of methanol and refluxed for 2 h 30min. After evaporation, the reaction medium is treated under the conditions described in Example 1(b). After recrystallization from absolute ethanol, 2.4 g (84%) of 4-[(Z)-2-(3-(1-adamantyl)-4-methoxyphenyl)propenyl]benzoic acid are isolated, which acid melts at 267° C.

EXAMPLE 24

Benzyl 4-[(E)-2-(3-(1-adamantyl)-4-methoxyphenyl)propenyl]benzoate.

2 g (5 mmol) of 4-[(Z)-2-(3-(1-adamantyl)-4-methoxyphenyl)propenyl]benzoic acid obtained in Example 23(c) in 900 ml of THF are irradiated under UV by means of a HANOVIA mercury lamp (550 W) for 10 h at room temperature, to give a 1/1 mixture of E and Z isomers. After evaporation of the THF, this mixture is treated with 190 mg (6 mmol) of 80% NaH in oil and 0.83 ml (7 mmol) of benzyl bromide. After the same treatment as in Example 1(a), followed by a recrystallization from hexane, 0.54 g of benzyl 4-[(E)-2-(3-(1-adamantyl)-4-methoxyphenyl)propenyl]benzoate is isolated which melts at 230°–240° C.

EXAMPLE 25

4-[(E)-2-(3-(1-adamantyl)-4-hydroxyphenyl)-1-propenyl] benzoic acid.

a) 3-(1-adamantyl)-4-tert-butyldimethylsilyloxyphenylethanone 14.5 g (37.5 mmol) of 3-(1-adamantyl)-4-tertbutyldimethylsilyloxybenzoic acid in 150 ml of ether are treated at −20° C. with 75 mmol of methyllithium (1.6M in Et$_2$O). The reaction mixture is left stirring at room temperature overnight, under nitrogen, it is then poured into ice cold water and extracted with 500 ml of ether. The organic phase is washed with water, dried over magnesium sulphate and evaporated to give, after chromatography on silica in the ether/hexane eluent (50/50), 12 g (83%) of the expected derivative which melts at 114.5° C.

b) 3-(1-Adamantyl)-4-tert-butyldimethylsilyloxyphenylethanol 11.5 g (30 mmol) of the derivative obtained in Example 25(a), in solution in 100 ml of THF, are treated with 1.1 g (30 mmol) of NaBH$_4$ for 2 h at room temperature. The reaction medium is evaporated, taken up in 100 ml of ether, washed with water, dried and evaporated to give 9 g (78%) of the expected product which melts at 71°–72° C.

c) 3-(1-Adamantyl)-4-tert-butyldimethylsilyloxyethylphosphonium bromide 9 g (23.3 mmol) of the derivative obtained in Example 25(b), in solution in 50 ml of methanol, are treated with 8.2 g (23.9 mmol) of triphenylphosphine hydrobromide and stirred under nitrogen at room temperature overnight. The reaction medium is evaporated and then the residue is triturated in ether to give 15.5 g (93%) of the expected derivative which melts at 221°–222° C.

d) Methyl 4-[(E)-2-(3-(1-adamantyl)-4-tert-butyldimethylsilyloxyphenyl)- 1-propenyl]benzoate 3 g (4.2 mmol) of the derivative obtained in Example 25(c), in solution in 50 ml of THF, are treated at −40° C. with 2.9 ml of n-butyllithium (1.6M in hexane). The reaction medium is allowed to return to 20° C. over 6 h and 690 mg (4.2 mmol) of methyl p-carboxaldehydebenzoate in 10 ml of THF are added and allowed to react under nitrogen, at room temperature, overnight. After the same treatment as for Example 1(a), followed by a recrystallization from heptane, 0.6 g of the expected derivative is isolated which melts at 144° C.

e) 4-[(E)-2-(3-(1-adamantyl)-4-hydroxyphenyl)-1-propenyl]benzoic acid 0.6 g (1.16 mmol) of the derivative obtained in Example 25(d), in solution in 5 ml of THF and 5 ml of methanol, are treated with 12 ml of 2N sodium hydroxide. The reaction is left stirring at room temperature for 24 h. After the same treatment as in Example 8, followed by a recrystallization from the cyclohexane/diisopropyl ether mixture, 150 mg (32%) of the expected derivative are isolated, which derivative melts at 245°–246° C.

EXAMPLE 26

6-[3-(1-Adamantyl)-4-methoxycarbonylphenyl]- 2-naphthylcarboxamide.

a) 6-[3-(1-adamantyl)-4-methoxycarbonylphenyl]-2-naphthoic acid chloride 2.1 g (4.77 mmol) of the acid obtained in Example 15, in 60 ml of toluene at 50° C., are treated with 0.70 ml (9.65 mmol) of thionyl chloride. The reaction mixture is heated at 110° C. for 6 h and then evaporated to dryness to give 2.22 g of the expected acid chloride.

b) 6-[3-(1-Adamantyl)-4-methoxycarbonylphenyl]-2-naphthylcarboxamide 0.74 g (1.61 mmol) of the acid chloride obtained in Example 26(a) is added dropwise to 10 ml of a 33% aqueous ammonium hydroxide solution. The reaction mixture is stirred at room temperature overnight and then poured into water and extracted with ethyl acetate. The organic phase is rinsed with water until the pH is neutral, dried over magnesium sulphate and evaporated. After chromatography on silica in the dichloromethane/methanol eluent (95/5), 347 mg (50%) of the expected derivative are isolated, which derivative melts at 270°–272° C.

EXAMPLE 27

Ethyl 4-[(E)-2-(3-(1-methylcyclohexyl)-4-hydroxyphenyl)propenyl]benzoate.

a) 3-(1-methylcyclohexyl)-4-tert-butyldimethylsilyloxyphenylethanone 28.82 g (0.083 mol) of 3-(1-methylcyclohexyl)-4-tert-butyldimethylsilyloxybenzoic acid, in 300 ml ether, are treated at −20° C. under nitrogen, with 0.166 mol of methyllithium (1.6M in ether). The reaction mixture is stirred under nitrogen overnight and it is then treated as for Example 25(a). After filtration of the residue on silica, 22 g (76%) of the expected product are isolated in the form of a yellow oil.

NMR (1H): δ ppm (CDCl$_3$) :0.36(6H,s); 1.04 (9H,s); 1.31 (3H,s); 1.47–1.75 (8H,m); 2.19 (2H,m); 2.56 (3H,s); 6.84 (1H,d); 7.71 (1H,d); 7.99 (1H,s).

b) Z and E isomers of ethyl 4-[2-(3-(1-methylcyclohexyl)-4-tert-butyldimethylsilyloxyphenyl)propenyl]benzoate The mixture consisting of 21 g (60 mmol) of the ketone obtained in Example 27(a), 21.6 g (60 mmol) of ethyl 4-ethoxycarbonylbenzylphosphonate and 2.64 g of crown ether (15-crown-5) in 400 ml of THF are added dropwise to a suspension of 2.16 g (72 mmol) of NaH (80% in oil) in 50 ml of THF, under argon. The reaction medium is stirred under nitrogen, at room temperature for 36 h. After the same treatment as in Example 23(b) (Wittig-Horner reaction), 10.5 g (35.5%) of the Z isomer and 2.52 g (8.5%) of the E isomer are isolated, each in the form of a yellowish oil.

7.92 g (16mmol) of the Z isomer are irradiated under UV, under the conditions described in Example 24, for 24 h to give a 1/1 mixture of Z and E isomers. After chromatography on silica in the hexane/ether eluent (97/3), 3.09 g of the ethyl 4-[(Z)-2-(3-(1-methylcyclohexyl)- 4-tert-butyldimethylsilyloxyphenyl)propenyl]benzoate are isolated in the form of an oil, and 2.7 g of ethyl 4-[(E)-2-(3-(1-methylcyclohexyl)-4-tert-butyldimethylsilyloxyphenyl)propenyl]benzoate in the form of an oil.

NMR (1H): Z Isomer δ ppm (CDCl$_3$): 0.30 (6H,s); 0.88 (6H,m); 1 (9H, s); 1.18 (2H,s); 1.23 (2H,m); 1.33 (3H,t); 1.99 (2H,m); 2.2 (3H,s); 4.30 (2H,q); 6.41 (1H,s); 6.88 (1H,d); 6.90 (1H,d); 6.92 (1H,s); 6.96 (2H,d); 7.74 (2H,d). E Isomer δ ppm (CDCl$_3$) 0.31 (6H,s); 0.85 (4H,m); 1 (9H,s); 1.24 (3H,s); 1.31 (2H,s); 1.38 (3H,t); 1.73 (2H,m); 2.15 (2H,m); 2.26 (3H,s); 4.36 (2H,q); 6.76 (1H,s); 6.79 (1H,d); 7.23 (1H,d); 7.39 (2H,d); 7.46 (1H,s); 8 (2H,d).

c) Ethyl 4-[(E)-2-(3-(1-methylcyclohexyl)-4-hydroxyphenyl)propenyl]benzoate 7.22 g (14.6 mmol) of the E isomer obtained in Example 27(b) in 40 ml of THF are treated with 16.5 mmol of tetrabutylammonium fluoride. The mixture is left stirring at room temperature for 1 h 30 min. After the same treatment as in Example 4(a), followed by a crystallization from hexane, 4.23 g (76%) of the expected derivative are isolated, which derivative melts at 131.2° C.

EXAMPLE 28

Ethyl 4-[(E)-2-(3-(1-methylcyclohexyl)-4-methoxyphenyl)propenyl]benzoate 2.20 g (5.84 mmol) of the phenol obtained in Example 27(c), in solution in 20 ml of dimethylformamide (DMF), are treated with 194 mg (6.42 mmol) of sodium hydride (80% in oil), then with 0.365 ml of methyl iodide. The reaction medium is stirred under nitrogen, at room temperature for 1 h 30 min and then treated as in Example 4 (a). After chromatography on silica in the dichloromethane/hexane eluent (60/40) and recrystallization from hexane, 1.56 g (81%) of the expected derivative are obtained, which derivative melts at 60°–62° C.

EXAMPLE 29

4-[(E)-2-(3-(1-methylcyclohexyl)-4-methoxyphenyl)propenyl]benzoic acid 1.71 g (4.36 mmol) of the derivative obtained in Example 28 are treated with 2.06 g of sodium hydroxide in 25 ml of methanol. The reaction medium is stirred for 24 h at room temperature and it is then refluxed for 1 h. After the same treatment as in Example 8, 1.20 g (75%) of the expected derivative is isolated, the derivative melts at 242°–244° C.

EXAMPLE 30

Ethyl 4-[(Z)-2-(3-(1-methylcyclohexyl)-4-hydroxyphenyl)propenyl]benzoate 2.20 g (4.46 mmol) of the Z isomer obtained in Example 27(b), in solution in 40 ml of THF, are treated with 4.91 mmol of tetrabutylammonium fluoride under the conditions described in Example 27(c), to give, after crystallization from hexane, 1.25 g (74%) of the expected derivative which melts at 123.5° C.

EXAMPLE 31

Ethyl 4-[(Z)-2-(3-(1-methylcyclohexyl)-4-methoxyphenyl)propenyl]benzoate 1.23 g (3.25 mmol) of the derivative obtained in Example 30, in solution in 15 ml of DMF, are treated with 533 mg of potassium carbonate and 0.75 ml of methyl iodide. The reaction medium is stirred at room temperature for 48 h and then heated at 50° C. for 24 h. After the same treatment as in Example 2(a), followed by a chromatography on silica in the hexane/ether eluent (95/5), 709 mg (56%) of the expected derivative are isolated in the form of a yellowish oil.

NMR (1H): δ ppm (CDCl$_3$): 1.1 (2H,m); 1.19 (3H,s); 1.25 (4H,m); 1.31 (3H,t); 1.34 (2H,m); 1.99 (2H,m); 2.22 (3H,s); 3.81 (3H,s); 4.31 (2H,q); 6.44 (1H,s); 6.80 (1H,d); 6.98 (4H,m); 7.76 (2H,d).

EXAMPLE 32

4-[(Z)-2-(3-(1-methylcyclohexyl)-4-methoxyphenyl)propenyl]benzoic acid 0.69 g (1.76 mmol) of the ester obtained in Example 31, in 15 ml of methanol, is treated with 1.58 g of sodium hydroxide. The reaction mixture is stirred at 40° C. for 2 h. After the same treatment as in Example 8, 462 mg (72%) of the expected derivative are isolated, which derivative melts at 175°–176° C.

EXAMPLE 33

Ethyl 4-[(Z)-2-(3-tert-butyl-4-methoxyphenyl)propenyl]benzoate a) 3-tert-butyl-4-methoxyphenylethanone 6.23 g (30mmol) of 3-tert-butyl-4-methoxyphenylbenzoic acid are treated with 48 ml of methyllithium (1.6 M in ether) under the conditions described in Example 25(a) to give 6.01 g (97%) of the expected derivative in the form of a yellowish oil.

NMR (1H): δ ppm (CDCl$_3$): 1.39 (9H,s); 2.56 (3H,s); 3.91 (3H,s); 6.89 (1H,d); 7.82 (1H,d); 7.94 (1H,d).

b) Ethyl 4-[(Z)-2-(3-tert-butyl-4-methoxyphenyl)propenyl]benzoate 6.01 g (29 mmol) of the ketone obtained in Example 33(a) are reacted with 10.5 g (35 mmol) of diethyl 4-ethoxycarbonylbenzylphosphonate under the conditions described in example 27(b), to give 3.86 g (38%) of the expected derivative in the form of a yellowish oil, and 5.42 g (53%) of the isomer ethyl 4-[(E)-2-(3-tert-butyl-4-methoxyphenyl)propenyl]benzoate which melts at 71.5° C.

NMR (1H): δ ppm (CDCl$_3$): 1.26 (9H,s); 1.32 (3H,t); 2.22 (3H,s); 3.85 (3H,s); 4.30 (2H,q); 6.44 (1H,s); 6.80 (1H,d); 7.03 (4H,m); 7.78 (2H,d).

EXAMPLE 34

4-[(Z)-2-(3-tert-butyl-4-methoxyphenyl)propenyl]benzoic acid;

1.21 g (3.43 mmol) of the Z isomer obtained in Example 33(b) in 20 ml of methanol are treated with 1.60 g of sodium hydroxide and refluxed for 1 h 30 min. After the same treatment as in Example 8, followed by a recrystallization from the ethanol/water mixture, 0.96 g (87%) of the expected derivative is isolated which melts at 182°–184° C.

EXAMPLE 35

4-[(E)-2-(3-tert-butyl-4-hydroxyphenyl)propenyl]benzoic acid 1.84 g of lithium methanethiolate are added to 2 g (5.67 mmol) of the E ester obtained in Example 33(b) in 40 ml of DMF. The reaction mixture is stirred under nitrogen at 120° C. for 4 h. After the same treatment as in Example 8, followed by a chromatography in the ether/hexane eluent (80/20), 1.69 g of a mixture of E and Z isomers of 4-[-2-(3-tert-butyl-4-hydroxyphenyl)propenyl]benzoic acid are isolated in the respective proportions (83:17). A recrystallization from the hexane/ether mixture gives 225 mg of the expected derivative which melts at 209° C.

EXAMPLE 36

4-[(E)-2-(3-(1-methylcyclohexyl)-4-hydroxyphenyl)ethenyl]benzoic acid a) 4-tert-butyldimethylsilyloxy-3-(1-methylcyclohexyl)benzaldehyde 1.54 g of magnesium are placed in a 500 ml three-necked round-bottomed flask and then a solution containing 22.09 g (57.7 mmol) of 4-tert-butyldimethylsilyloxy- 3-(1-methylcyclohexyl)bromobenzene is added through a dropping funnel. The reaction is activated by a few drops of dibromoethane. 4.45 ml (57 mmol) of DMF are then added and the mixture is left stirring for 30 min at room temperature. The reaction medium is poured into water and then extracted with ethyl acetate. After rinsing the organic phase with water, drying over magnesium sulphate, evaporation and chromatography on silica in the dichloromethane/hexane eluent (50/50), 16 g (84%) of the expected derivative are isolated.

NMR (1H): δ ppm (CDCl$_3$): 0.34 (6H,s); 1.02 (9H,s); 1.29 (3H,s); 1.41–1.73 (8H,m); 2.08 (2H,m); 6,88 (1H,d); 7.60 (1H,d); 7.83 (1H,d).

b) Ethyl 4-[(E)-2-(3-(1-methylcyclohexyl)-4-tert-butyldimethylsilyloxyphenyl)ethenyl]benzoate 5 g of the aldehyde obtained in Example 36(a) and 4.52 g (15.06 mmol) of diethyl ethoxycarbonylbenzylphosphonate in solution in 45 ml of THF are treated with 0.45 g of sodium hydride (80% in oil) and 0.05 ml of 15-crown-5, under the conditions described in Example 27(b). After the same treatment and chromatography on silica in the dichloromethane/hexane eluent (20/80), 4 g (56%) of the expected derivative are isolated, which derivative melts at 88.7° C.

c) Ethyl 4-[(E)-2-(3-(1-methylcyclohexyl)-4-hydroxyphenyl)ethenyl]benzoate 3.59 g (7.5 mmol) of the derivative obtained in Example 36(b), in solution in 35 ml of THF, are treated with 7.5 ml of tetrabutylammonium fluoride, under the conditions described in Example 27(c), to give, after the same treatment followed by a treatment in hexane, 2.1 g (77%) of the expected derivative which melts at 148.6° C.

d) 4-[(E)-2-(3-(1-methylcyclohexyl)-4-hydroxyphenyl)ethenyl]benzoic acid 508 mg (1.39 mmol) of the ester obtained in Example 36(c) in 10 ml of methanol are treated with 1.05 g of sodium hydroxide. The reaction mixture is refluxed for 45 min and it is then treated as indicated in Example 8. After recrystallization from the diisopropylether/hexane mixture, 265 mg (57%) of the expected derivative are isolated, which derivative melts at 229° C.

EXAMPLE 37

Ethyl 4-[(E)-2-(3-(1-methylcyclohexyl)-4-(6-tert-butoxycarbonylpentyloxy)phenyl)ethenyl]benzoate 1.57 g (4.34 mmol) of the phenol obtained in Example 36(c), in 30 ml of DMF, are treated with 1.3 g (5.19mmol) of tert-butyl 6-bromohexanoate and 0.717 g of potassium carbonate. The reaction mixture is stirred at 60° C. for 50 h. After the same treatment as in Example 1(a), the residue is chromatographed in the ether/hexane eluent (15/85) and then recrystallized from hexane to give 1.17 g (51%) of the expected derivative which melts at 90°–91° C.

EXAMPLE 38

Ethyl 4-[(E)-2-(3-(1-methylcyclohexyl)-4-(6-carboxypentyloxy)phenyl)ethenyl]benzoate 0.73 g (1.37 mmol) of the diester obtained in Example 37, in solution in 30 ml of carbon tetrachloride, are treated with 0.23 ml (1.64 mmol) of trimethylsilyl iodide. The reaction mixture is left stirring and under nitrogen for 18 h at room temperature. After the same treatment as in Example 1, followed by a chromatography on silica in the elution gradient from dichloromethane to the dichloromethane/ether mixture (95/5), 0.47 g (72%) of the expected product is obtained which melts at 112°–114° C.

EXAMPLE 39

4-[(E)-2-(3-(1-adamantyl)-4-hydroxyphenyl)ethenyl]benzoic acid a) 4-tert-butyldimethylsilyloxy-3-(1-adamantyl)benzaldehyde 2.6 g of magnesium and 0.05 ml of dibromoethane are added to 33 g (78 mmol) of 3-(1-adamantyl)-4-tertbutyldimethylsilyloxybromobenzene in 300 ml of THF and then the mixture is refluxed for 3 h 30 min under nitrogen After cooling the mixture to 0° C., 5.8 ml of anhydrous DMF are then added and the mixture is left stirring for 1 h at room temperature. After evaporation, the residue is taken up in 100 ml of water, acidified up to pH 5, extracted with ether and the organic phase is washed with water and dried over magnesium sulphate. 22.3 g (77%) of the expected derivative are isolated, which derivative melts at 121°–122° C.

b) Ethyl 4-[ (E)-2-(3-(1-adamantyl)-4-tert-butyldimethylsilyloxyphenyl)ethenyl]benzoate 3.7 g (10 mmol) of the aldehyde obtained in Example 39(a), 3 g of diethyl 4-ethoxycarbonylbenzylphosphonate and 44 mg of 15-crown-5 are added to a suspension of 290 mg of sodium hydride (80% in oil) in 50 ml of THF. The reaction medium is stirred under nitrogen at room temperature overnight. After the same treatment as in Example 27(b) followed by a chromatography on silica in the ether/hexane eluent (20/80), 2.4 g (46%) of the expected derivative are isolated, which derivative melts at 112°–113° C.

c) 4-[(E)-2-(3-(1-adamantyl)-4-hydroxyphenyl)ethenyl] benzoic acid 2.4 g (4.6 mmol) of the ester obtained in Example 39(b), in 25 ml of methanol, are treated with 1.84 g of sodium hydroxide. The mixture is refluxed for 6 h to give, after the same treatment as in Example 3 followed by a chromatography on silica in the ether/hexane eluent (60/40), 1.26 g (73%) of the expected derivative which melts at 279°–280° C.

EXAMPLE 40

Benzyl 6-[3-(1-adamantyl)-4-(1,2-dihydroxyethyl)phenyl]-2-naphthoate;

a) Benzyl 6-[3-(1-adamantyl)-4-ethenylphenyl]-2-naphthoate 13.8 g (22 mmol) of the derivative obtained in Example 18(a) in 280 ml of DMF are treated with 9.4 ml (31 mmol) of alkyltributyltin, 2.83 g of lithium chloride and 515 mg (0.7 mmol) of $PdCl_2(P(C_6H_5)_3)_2$. The reaction mixture is heated under nitrogen at 80° C. overnight and then 154 mg of catalyst and 3.9 ml of vinyltributyltin are added and again heated at 80° C. for 48 h. After the same treatment as in Example 20(a) followed by a chromatography on silica in the dichloromethane/hexane eluent (30/70), 4.54 g (41%) of the expected derivative are isolated, which derivative melts at 158°–160° C.

b) Benzyl 6-[3-(1-adamantyl)-4-(1,2-dihydroxyethyl)phenyl]- 2-naphthoate 2.5 g (5 mmol) of the derivative obtained in Example 40 (a) in 5 ml of water, 15 ml of tert-butanol and 0.4 ml of pyridine are treated with 760 mg (6.8 mmol) of trimethylamine N-oxide and 25 mg of osmiumtetroxide. The reaction mixture is refluxed for 6 h and it is then left stirring overnight at room temperature. 4 ml of sodium hydrogen sulphite (2M) and 20 ml of water are added to the reaction medium and then extracted with ethyl acetate. The organic phase is rinsed with water, dried over magnesium sulphate and evaporated. After chromatography on silica in the dichloromethane/ether eluent (90/10), 1.92 g (72%) of the expected derivative are isolated, which derivative melts at 193° C.

EXAMPLE 41

6-[3-(1-Adamantyl)-4-(1,2-dihydroxyethyl)phenyl]-2-naphthoic acid;

0.6 g of palladium on carbon (10%) is added to 1.90 g (3.57 mmol) of the benzyl ester obtained in Example 40(b) in 50 ml of dioxane. The mixture is stirred under a hydrogen pressure of 7 bar at 50° C. for 4 h. After the same treatment as in Example 5 followed by a recrystallization from the ethanol/water mixture, 1.20 g (76%) of the expected derivative are isolated, which derivative melts at 239° C.

EXAMPLE 42

Benzyl 6-[3-(1-adamantyl)-4-(3-hydroxypropyl)phenyl]-2-naphthoate 5.13 g (10 mmol) of the derivative obtained in Example 20(a), in solution in 20 ml of THF, are treated at 0° C. by addition, dropwise, of 15 mmol of 9-borabicyclo[3.3.1] nonane (0.5 M/THF). The reaction mixture is stirred under nitrogen for 1 h at 0° C. and 1 h at room temperature. 25 ml of sodium hydroxide (1M) and 20 ml of hydrogen peroxide (30%) are then added at 0° C. and the mixture is left stirring at 0° C. for 1 h and then for 2 h at room temperature. After evaporation of the THF and extraction with dichloromethane (3×100 ml), the organic phase is washed, dried over magnesium sulphate and then evaporated. After chromatography on silica in the dichloromethane/hexane eluent (80/20), 4.67 g (88%) of the expected derivative are isolated, which derivative melts at 176° C.

EXAMPLE 43

6-[3-(1-Adamantyl)-4-(3-hydroxypropyl)phenyl]-2-naphthoic acid 2.67 g (5 mmol) of the ester obtained in Example 42, in solution in 50 ml of dioxane, are stirred under a hydrogen pressure of 7 bar for 7 h at room temperature and then for 1 h at 50° C. in the presence of 800 mg of palladium on carbon (10%). After the same treatment as in Example 5 followed by a recrystallization from the ethanol/water mixture, 1.78 g (81%) of the expected derivative are isolated, which derivative melts at 262.4° C.

EXAMPLE 44

Benzyl 6-[3-(1-adamantyl)-4-(3-acetoxypropyl)phenyl]-2-naphthoate;

2 g (3.77 mmol) of the derivative obtained in Example 42, in solution in 40 ml of THF, are treated with 0.8 ml of triethylamine and 0.4 ml of acetyl chloride. The reaction mixture is left stirring overnight at room temperature and it is then poured into water, extracted with ether, washed with a saturated aqueous sodium bicarbonate solution and then dried over magnesium sulphate. After chromatography on silica in the dichloromethane/hexane eluent (60/40), 1.78 g (82%) of the expected derivative are obtained, which derivative melts at 132° C.

EXAMPLE 45

6-[3-(1-Adamantyl)-4-(3-acetoxypropyl)phenyl]-2-naphthoic acid 1.77 g (3.1 mmol) of the diester obtained in Example 44, in solution in 50 ml of dioxane, are hydrogenated in the presence of 530 mg of palladium on carbon (10%) at 50° C., under a hydrogen pressure of 7 bar. After the same treatment as in Example 5 followed by a recrystallization from ethyl acetate, 1.13 g (83%) of the expected product are isolated, which product melts at 260° C.

EXAMPLE 46

Benzyl 6-[3-(1-adamantyl)-4-(2,3-dihydroxypropyl)phenyl]-2-naphthoate 5.13 g (10 mmol) of the derivative obtained in Example 20(a) in 9 ml of water, 30 ml of tert-butanol and 0.8 ml of pyridine are treated with 1.51 g (136 mmol) of trimethylamine N-oxide and 20 mg of osmium tetroxide. The reaction mixture is refluxed for 24 h. After the same treatment as in Example 40(b) followed by a chromatography on silica in an elution gradient from the dichloromethane/ether mixture from (9:1) to (7:3), 4 g (74%) of the expected derivative are isolated, which derivative melts at 199.5° C.

EXAMPLE 47

6-[3-(1-Adamantyl)-4-(2,3-dihydroxypropyl)phenyl]-2-naphthoic acid 4 g (7.32 mmol) of the ester obtained in Example 46, in solution in 100 ml of dioxane, are hydrogenated in the presence of 1.20 g of palladium on carbon (10%) under a hydrogen pressure of 7 bar, for 5 h at 50° C. After the same treatment as in Example 5, followed by a recrystallization from the ethanol/water mixture, 3 g (90%) of the expected derivative are isolated, which derivative melts at 258° C.

EXAMPLE 48

N-methoxycarbonylmethyl-4-(6-benzyloxycarbonylnaphthyl)- 2-(1-adamantyl)phenylcarboxamide 3.14 g (5 mmol) of the triflate obtained in Example 18(a), in 60 ml of DMF, are treated with 2.80 ml (20 mmol) of triethylamine, 57 mg of palladium acetate, 280 mg of DPPF and 1.27 g (10 mmol) of glycine methyl ester in the form of its hydrochloride. The reaction medium is heated at 80° C. under a carbon monoxide pressure of 3 bar for 16 h. After the same treatment as in Example 20(a) followed by a chromatography on silica in dichloromethane, 1.25 g (43%) of the expected derivative are isolated, which derivative melts at 116°–117° C.

EXAMPLE 49

N-methoxycarbonylmethyl-4-(6-carboxynaphthyl)- 2-(1-adamantyl)phenylcarboxamide 1.25 g (2.1mmol) of the benzyl ester obtained in Example 48, in 50 ml of dioxane, are hydrogenated at 70° C. in the presence of 190 mg of palladium on carbon (10%), under a hydrogen pressure of 7 bar, for 12 h. After the same treatment as in Example 5 followed by a recrystallization from the ethyl acetate/hexane mixture, 742 mg (71%) of the expected derivative are isolated, which derivative melts at 272° C.

EXAMPLE 50

6-[3-(1-Adamantyl)-4-(N,N-dimethylcarbamoyl)phenyl]-2-naphthoic acid 3.40 g (7.4 mmol) of the acid chloride obtained in Example 10, prepared as indicated in Example 26(a), are placed in 10 ml of hexammethylphosphoramide and are treated with 56 mg of $(C_6H_5)CH_2Pd(P(C_6B_5)_3)_2Cl$ and stirred under nitrogen at 65° C. for 3 days. After the same treatment as in Example 20(a) followed by a chromatography on silica in the dichloromethane/hexane elution gradient from (60:40) to (90:10), 1 g (29%) of the benzyl 6-[3-(1-adamantyl)-4-(N,N-dimethylcarbamoyl)phenyl]-2-naphthoate derivative is isolated.

990 mg (2.11 mmol) of this ester, in 25 ml of methanol, are treated with 2 g of sodium hydroxide. The reaction mixture is refluxed for 1 h and it is then treated as in Example 3. After recrystallization from absolute ethanol, 630 mg (66%) of the expected product are isolated, which product melts at 318°–320° C.

EXAMPLE 51

Benzyl 6-[3-(1-adamantyl)-4-(2(R),3-dihydroxypropyloxy)phenyl]-2-naphthoate a) Benzyl 6-[3-(1-adamantyl)-4-(2,2-dimethyl-1,3-dioxolane- 4(R)-methyloxy)phenyl]-2-naphthoate 9.76 g (20 mmol) of the phenol obtained in Example 4(a), in 60 ml of DMF, are treated successively with 604 mg (20 mmol) of sodium hydride (80% in oil) and then with 6.86 g (24 mmol) of (2R)-3-tosyloxy-1,2-propanediol acetonide. The reaction mixture is stirred under nitrogen at room temperature for 24 h. After the same treatment as in Example 1(a) followed by a chromatography on silica in the hexane/acetone/dichloromethane elution gradient from (75:5:20) to (80:10:10), 8.35 g (69%) of the expected derivative are isolated, which derivative melts at 170°–172° C.

b) Benzyl 6-[3-(1-adamantyl)-4-(2(R),3-dihydroxypropyloxy)phenyl]-2-naphthoate 4.80 g (7.96 mmol) of the acetonide obtained in Example 51(a) are suspended in 100 ml of an aqueous formic acid solution (40%). The reaction mixture is heated at 100° C. for 5 h and it is then stirred over one weekend at room temperature. After the same treatment as in Example 18(b) followed by a chromatography on silica in the dichloromethane/ethyl acetate elution gradient from (90:10) to (80:20) and a recrystallization from the ether/hexane mixture, 3.46 g (77%) of the expected derivative are isolated, which derivative melts at 204° C.

EXAMPLE 52

6-[3-(1-Adamantyl)-4-(2(R),3-dihydroxypropyloxy)phenyl]-2-naphthoic acid 3.45 g (6 mmol) of the benzyl ester obtained in Example 51, in 50 ml of methanol, are treated with 4 g of sodium hydroxide. The reaction medium is refluxed for 2 h and it is then treated as indicated in Example 6. After a recrystallization from the ethanol/water mixture, 2.28 g (87%) of the expected derivative are isolated, which derivative melts at 271°–272° C., $[\alpha]_D=+1.5°$ (c=1,DMF).

EXAMPLE 53

6-[3-(1-Adamantyl)-4,5-methylenedioxyphenyl]- 2-naphthoic acid a) 3-(1-adamantyl)-4,5-methylenedioxybromobenzene 4.82 g (24.9 mmol) of acetoxyadamantane and 0.75 ml (139 mmol) of concentrated sulphuric acid are added to 5 g (24.9 mmol) of 3,4-methylenedioxybromobenzene in 35 ml of cyclohexane and 35 ml of heptane. The reaction medium is stirred at room temperature overnight. This medium is then hydrolyzed with 250 ml of water, neutralized with sodium bicarbonate, extracted with 200 ml of dichloromethane, dried over magnesium sulphate and evaporated, to give 2.89 g (34.8%) of the expected derivative which melts at 134° C.)

b) Methyl 6-[3-(1-adamantyl)-4,5-methylenedioxyphenyl]-2-naphthoate 2.75 g (8.21 mmol) of the derivative obtained in Example 53(a), in 10 ml of THF, are treated at −76° C. with 3.61 ml of n-butyllithium (2.5 M/hexane), the mixture is allowed to return to the temperature of 0° C. and then 0.44 g (3.28 mmol) of zinc chloride is added and the mixture is left stirring for 15 min under nitrogen and then 0.53 g (1.99 mmol) of methyl 6-bromo-2-naphthoate is added. The reaction mixture is left starring for 2 h at room temperature and it is then treated as in Example 2(b). After chromatography on silica in the hexane/ethyl acetate eluent (85/5), 1.25 g (38%) of the expected derivative are isolated, which derivative melts at 217°–220° C.

c) 6-[3-(1-Adamantyl)-4,5-methylenedioxyphenyl]-2-naphthoic acid 150 mg (0.341 mmol) of the ester obtained in Example 53(b), in 3 ml of n-butanol, are treated with 45 mg of potassium hydroxide and stirred at 80° C. for 1 h. After the same treatment as in Example 3, the residue is triturated in hexane. The precipitate is then dried to give 123.5 mg (85%) of the expected derivative which melts at 300°–305° C.

EXAMPLE 54

N-ethyl 6-[3-(1-adamantyl)-4-methoxycarbonylphenyl]-2-naphthylcarboxamide 0.74 g (1.61 mmol) of the acid chloride prepared in Example 26(a) is added to 10 ml of a 70% aqueous ethylamine solution and the mixture is stirred at room temperature overnight. After the same treatment as in Example 26(b) followed by a chromatography on silica in dichloromethane, 440 mg (58%) of the expected derivative are isolated, which derivative melts at 201.9° C.

EXAMPLE 55

N,N-morpholyl 6-[3-(1-adamantyl)-4-methoxycarbonylphenyl]-2-naphthylcarboxamide 0.74 g (1.61 mmol) of the acid chloride 26(a) is added to a solution of 0.28 ml (3.22 mmol) of morpholine in 10 ml of THF containing 0.22 ml of triethylamine and the mixture is stirred at room temperature overnight. After the same treatment as in Example 26(b) followed by a chromatography on silica in the dichloromethane/ether mixture (90/10), 377 mg (46%) of the expected derivative are isolated, which derivative melts at 152° C.

EXAMPLE 56

4-[(E)-2-(3-tert-butyl-4-methoxyphenyl)propenyl]phenyl-carbinol 1.41 g (4.35 mmol) of the acid obtained in Example 29 are treated with 330 mg of lithium aluminium hydride. The reaction mixture is refluxed for 2 h 30 min and it is then treated with a saturated ammoniumchloride solution and then extracted with 300 ml of ether. After drying and evaporation of the organic phase, the residue is recrystallized from hexane to give 1.21 g (90%) of the expected derivative which melts at 88°–90° C.

EXAMPLE 57

4-(E)-2-(3-tert-butyl-4-methoxyphenyl)propenyl]benzylacetate.

800 mg (2.58 mmol) of the alcohol obtained in Example 56, in solution in 10 ml of pyridine, are treated with 0.28 ml of acetyl chloride and are allowed to react for 1 h at room temperature. After the same treatment as in Example 44 followed by a chromatography on silica in the dichloromethane/hexane mixture (50/50), 880 mg (97%) of the expected derivative are isolated in the form of a colourless oil.

NMR (1H): δ ppm (CDCl$_3$): 1.41 (9H,s); 2.11 (3H,s); 2.26 (3H,s); 3.86 (3H,s); 5.11 (2H,s); 6.75 (1H,s); 6.87 (1H,d); 7.35 (5H,m); 7.46 (1H,d).

EXAMPLES OF FORMULATIONS

A. ORAL ADMINISTRATION (a) 0.2 g tablet

Compound of Example 8 . . . 0.001 g

Starch . . . 0.114 g

Bicalciumphosphate . . . 0.020 g

Silica . . . 0.020 g

Lactose . . . 0.030 g

Talc . . . 0.010 g

Magnesium stearate . . . 0.005 g

In this example, the compound of Example 8 may be replaced by the same quantity of the compound of Example 13.

(b) Suspension to be taken orally, in 5 ml ampoules

Compound of Example 3 . . . 0.500 g

Glycerin . . . 0.500 g

Sorbitol at 70% . . . 0.500 g

Sodium saccharinate . . . 0.010 g

Methyl para-hydroxybenzoate . . . 0.040 g

Flavouring qs

Purified water . . . qs . . . 5 ml

In this example, the compound of Example 3 may be replaced with the same quantity of the compound of Example 19.

(c) 0.8 g tablet

Compound of Example 22 . . . 0.500 g

Pregelatinized starch . . . 0.100 g

Microcrystalline cellulose . . . 0.115 g

Lactose . . . 0.075 g

Magnesium stearate . . . 0.010 g

In this example, the compound of Example 22 may be replaced by the same quantity of the compound of Example 15.

(d) Suspension to be taken orally, in 10 ml ampoules

Compound of Example 5 . . . 0.200 g

Glycerin . . . 1.000 g

Sorbitol at 70% . . . 1.000 g

Sodium saccharinate . . . 0.010 g

Methyl para-hydroxybenzoate . . . 0.080 g

Flavouring qs

Purified water . . . qs . . . 10 ml

B. TOPICAL ADMINSTRATION (a) Ointment

Compound of Example 8 . . . 0.020 g
  Isopropyl myristate . . . 81.700 g
  Fluid vaseline oil . . . 9.100 g
  Silica sold by the company DEGUSSA under the name "Aerosil 200" . . . 9.180 g In this example, the compound of Example 8 may be replaced by the same quantity of the compound of Example 13.

(b) Ointment

Compound of Example 3 . . . 0.300 g
  White vaseline codex . . . qs . . . 100 g

In this example, the compound of Example 3 may be replaced by the same quantity of the compound of Example 19.

(c) Non-ionic water-in-oil cream

Compound of Example 22 . . . 0.100 g
  Mixture of emulsifying lanolin alcohols, and of refined waxes and oils, sold by the company BDF under the name "Eucerine anhydre" . . . 39.900 g
  Methyl para-hydroxybenzoate . . . 0.075 g
  Propyl para-hydroxybenzoate . . . 0.075 g
  Sterile demineralized water . . . qs . . . 100 g In this example, the compound of Example 22 may be replaced by the same quantity of the compound of Example 15.

(d) Lotion

Compound of Example 5 . . . 0.100 g
  Polyethylene glycol (PEG 400) . . . 69.900 g
  Ethanol 95% . . . 30.000 g (e) Hydrophobic ointment Compound of Example 6 . . . 0.300 g
  Isopropyl myristate . . . 36.400 g
  Silicone oil sold by the company Rhône Poulenc under the name "Rhodorsil 47 V 300" . . . 36.400 g
  Beeswax . . . 13.600 g
  Silicone oil sold by the company Goldschmidt under the name "Abil 300.000 cst" . . . qs . . . 100 g (f) Non-ionic oil-in-water cream Compound of Example 18 . . . 1.000 g
  Cetyl alcohol . . . 4.000 g
  Glycerol monostearate . . . 2.500 g
  PEG 50 stearate . . . 2.500 g
  Karite butter . . . 9.200 g
  Propylene glycol . . . 2.000 g
  Methyl para-hydroxybenzoate . . . 0.075 g
  Propyl para-hydroxybenzoate . . . 0.075 g
  Sterile demineralized water . . . qsp . . . 100 g

TABLE I

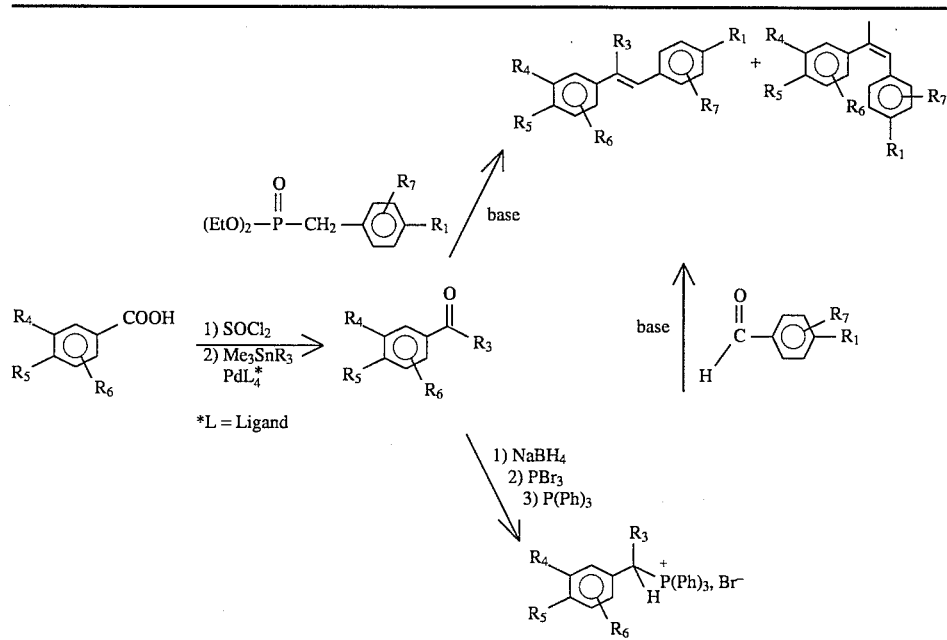

TABLE II

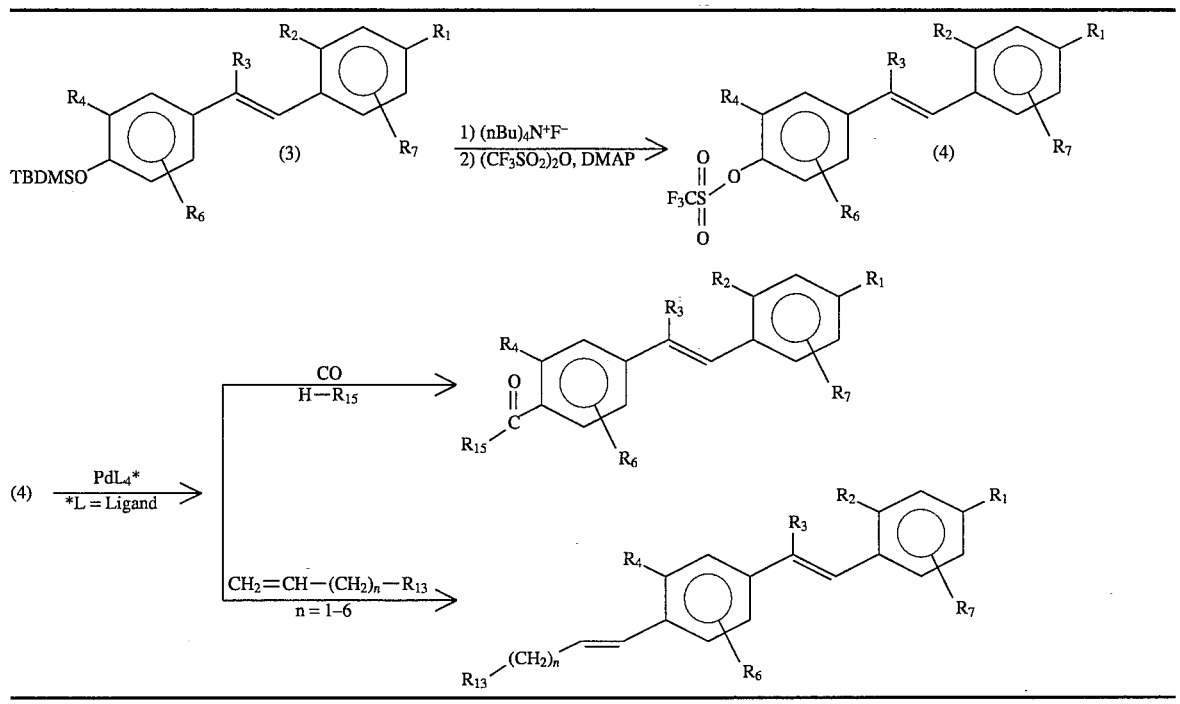

I claim:

1. Aromatic bicyclic compounds corresponding to the following formula:

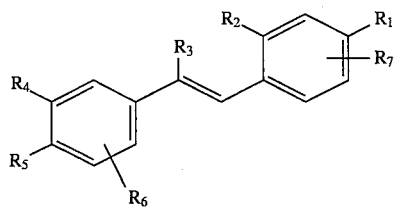

in which:

$R_1$ represents
(i) a hydrogen atom,
(ii) the radical —$CH_3$,
(iii) the radical —$CH_2$—O—$R_8$, $R_8$ representing a hydrogen atom or a lower alkyl radical having 1 to 6 carbon atoms,
(iv) a radical —$OR_8$,
(v) a radical

$R_{10}$ representing:
(a) a hydrogen atom,
(b) a radical

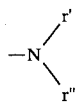

r' and r" representing a hydrogen atom, a lower alkyl radical, a mono- or polyhydroxyalkyl radical, an aryl radical, an aryl radical substituted by at least an halogen atom, a hydroxyl or a nitro function, an amino acid residue derived from lysine glycine or aspartic acid or a sugar residue derived from glucose, galactose or mannose or r' and r" taken together, form a heterocycle, selected from the group consisting of piperidino, morpholino, pyrrolidino and piperazino optionally substituted in the 4-position by a $C_1$-$C_4$ alkyl radical or a mono- or polyhydroxy radical (c) a radical —$OR_{11}$, $R_{11}$ representing a hydrogen atom, a linear or branched alkyl radical having 1 to 20 carbon atoms, a mono- or polyhydroxyalkyl radical, an aryl or aralkyl radical optionally substituted or a sugar residue or an amino acid residue as above defined, and (vi) a radical —$S(O)_tR_8$, t being 0, 1, or 2 and $R_8$ being as defined above, $R_2$ represents a hydrogen atom, $R_3$ represents a hydrogen atom, an aryl radical, an aralkyl radical or a lower alkyl radical optionally substituted by a hydroxyl, by a lower alkoxy or by a radical

$R_{12}$ representing a hydrogen atom, a lower alkyl radical, a hydroxyl radical, a lower alkoxy radical or a radical

or $R_2$ and $R_3$, taken together, form, with the benzene nucleus, a naphthalene ring, $R_4$ represents a linear branched or unbranched alkyl radical having 1 to 15 carbon atoms or a cycloaliphatic radical, $R_5$ represents the radical $-(CH_2)_n-R_{13}$, the radical $-CH=CH-(CH_2)_n-R_{13}$, or the radical $-O(CH_2)_m R_{14}$ n being 0 or 1 to 6, m being 1 to 6

$R_{13}$ representing the radical

a monohydroxyalkyl radical or a polyhydroxyalkyl radical the hydroxy functions being optionally protected in the methoxy or acetoxy form, an epoxy lower alkyl radical or the radical

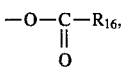

$R_{15}$ representing the radical $OR_{16}$ or the radical

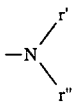

$R_{16}$ representing a hydrogen atom, a lower alkyl radical, an aryl radical or an aralkyl radical, $R_{14}$ representing a hydroxyl radical when m>2, a monohydroxyalkyl radical, a polyhydroxyalkyl radical, the radical

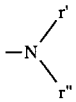

the radical

or a mono- or polyhydroxylated alkenyl radical having 2 to 10 carbon atoms, or when $R_2$ and $R_3$ are not taken together, m may be 0 and/or $R_{14}$ may represent a hydrogen atom or a lower alkyl radical, $R_6$ and $R_7$ represent a hydrogen atom, a halogen atom, a lower alkyl radical or the radical $-OR_{16}$, $R_5$ and $R_6$ may, in addition, form a methylenedioxy ring when $R_6$ is in the 3-position of the benzene nucleus, and the salts of the compounds of formula (I) when $R_1$ represents a carboxylic acid functional group and the chiral analogues of the said compounds of formula (I) and the geometrical isomers of the said compounds when $R_2$ and $R_3$ are not taken together.

2. The compounds according to claim 1, which are in the form of salts of an alkali or alkaline-earth metal or alternatively of zinc or of an organic amine.

3. The compounds according to claim 1, which are in the form of salts of an inorganic or organic acid selected from the group consisting of hydrochloric acid, sulphuric acid, acetic acid, citric acid, fumaric acid, hemisuccinic acid, maleic acid and mandelic acid.

4. The compounds according to claim 1, wherein the lower alkyl radical is 1 to 6 carbon atoms and is selected from the group consisting of methyl, ethyl, isopropyl, butyl and tert-butyl radicals.

5. The compounds according to claim 1 wherein the lower alkoxy radical is selected from the group consisting of a methoxy, ethoxy, isopropoxy and butoxy radical.

6. The compounds according to claim 1, wherein the cycloaliphatic radical is selected from the group consisting of the 1-methylcyclohexyl radical and 1-adamantyl radical.

7. The compounds according to claim 1, wherein the monohydroxyalky radical is selected from the group consisting of hydroxymethyl, 2-hydroxyethyl, 2-hydroxypropyl, 3-hydroxypropyl, 4-hydroxybutyl, 5-hydroxypentyl and 6-hydroxyhexyl radical.

8. The compounds according to claim 1, wherein the polyhydroxyalkyl radical comprises 3 to 6 carbon atoms and 2 to 5 hydroxyl groups and is selected from the group consisting of the 2,3-dihydroxypropyl, 2,3,4-trihydroxybutyl and 2,3,4,5-tetrahydroxypentyl radical and the pentaerythritol residue.

9. The compounds according to claim 1, wherein the aryl radical is a phenyl radical or a phenyl radical substituted by at least one halogen atom, a hydroxyl or a nitro functional group.

10. The compounds according to claim 1, wherein the aralkyl radical is the benzyl or phenethyl radical optionally substituted by at least one halogen atom, a hydroxyl or a nitro functional group.

11. A pharmaceutical composition, comprising in a vehicle suitable for an enteral, parenteral, topical or ocular administration, at least one compound of formula (I) according to claim 1.

12. A composition according to claim 1, containing from 0.001 to about 5% by weight of a compound of formula (I).

13. A cosmetic composition for body and hair care containing in a suitable cosmetic vehicle, at least one compound of formula (I) according to claim 1.

14. The cosmetic composition according to claim 13 containing the compound of formula (I) at a concentration of between 0.001 and 3%.

15. The compounds according to claim 1, which are selected from the group consisting of:

6-[3-(1-Adamantyl)-4-(3-aminopropyloxy)phenyl]-2-naphthoic acid hydrochloride;

Methyl 6-[3-(1-adamantyl)-4-(2,3-dihydroxypropyloxy)-phenyl]- 2-naphthoate;

6-[3-(1-Adamantyl)-4-(2,3-dihydroxypropyloxy)phenyl]-2-naphthoic acid;

Benzyl 6-[3-(1-adamantyl)-4-methoxycarbonylmethyloxyphenyl]- 2-naphthoate;

6-[3-(1-Adamantyl)-4-methoxycarbonylmethyloxyphenyl]-2-naphthoic acid;

6-[3-(1-Adamantyl)-4-carboxymethyloxyphenyl]-2-naphthoic acid;

Methyl 6-[3-(1-adamantyl)-4-(3-hydroxypropyloxy)phenyl] -2-naphthoate;

6-[3-(1-Adamantyl)-4-(3-hydroxypropyloxy)phenyl]-2-naphthoic acid;

Methyl 6-[3-(1-adamantyl)-4-benzyloxycarbonylphenyl]-2-naphthoate;

Methyl 6-[3-(1-adamantyl)-4-carboxyphenyl]-2-naphthoate;

Methyl 6-[3-(1-adamantyl)-4-hydroxymethylphenyl]-2-naphthoate;

6-[3-(1-Adamantyl)-4-hydroxymethylphenyl]-2-naphthoic acid;

6-[3-(1-Adamantyl)-4-acetoxymethylphenyl]-2-naphthoic acid;

Methyl 6-[3-(1-adamantyl)-4-methoxycarbonylphenyl]-2-naphthoate;

6-[3-(1-adamantyl)-4-methoxycarbonylphenyl]-2-naphthoic acid;
6-[3-(1-Adamantyl)-4-carboxyphenyl]-2-naphthoic acid;
6-[3-(1-Adamantyl)-4-carboxamidophenyl]-2-naphthoic acid;
Benzyl 6-[3-(1-adamantyl)-4-methoxycarbonylethenylphenyl]-2-naphthoate;
6-[3-(1-Adamantyl)-4-(methoxycarbonylethyl)phenyl]-2-naphthoic acid;
Benzyl 6-[3-(1-adamantyl)-4-(2,3-epoxypropyl)phenyl]-2-naphthoate;
6-[3-(1-Adamantyl)-4-(2-hydroxypropyl)phenyl]-2-naphthoic acid;
6-[3-(1-Adamantyl)-4-(3-methoxy-2-hydroxypropyl)phenyl]-2-naphthoic acid;
4-[(E)-2-(3-(1-adamantyl)-4-methoxyphenyl)propenyl]benzoic acid;
Benzyl 4-[(E)-2-(3-(1-adamantyl)-4-methoxyphenyl)propenyl]benzoate;
4-[(E)-2-(3-(1-adamantyl)-4-hydroxyphenyl)-1-propenyl]benzoic acid;
6-[3-(1-Adamantyl)-4-methoxycarbonylphenyl]-2-naphthylcarboxamide;
Ethyl 4-[(E)-2-(3-(1-methylcyclohexyl)-4-hydroxyphenyl)propenyl)benzoate;
Ethyl 4-[(E)-2-(3-(1-methylcyclohexyl)-4-methoxyphenyl)propenyl]benzoate;
4-[(E)-2-(3-(1-methylcyclohexyl)-4methoxyphenyl)propenyl]benzoic acid;
Ethyl 4-[(Z)-2-(3-(1-methylcyclohexyl)-4-hydroxyphenyl)propenyl)benzoate;
Ethyl 4-[(Z)-2-(3-(1-methylcyclohexyl)-4-methoxyphenyl)propenyl]benzoate;
4-[(Z)-2-3-(1-methylcyclohexyl)-4-methoxyphenyl)propenyl]benzoic acid;
Ethyl 4-[(Z)-2-(3-tert-butyl-4-methoxyphenyl)propenyl]benzoate;
4-[(Z)-2-(3-tert-butyl-4-methoxyphenyl)propenyl]benzoic acid;
4-[(E)-2-(3-tert-butyl-4-hydroxyphenyl)propenyl]benzoic acid;
4-[(E)-2-(3-(1-methylcyclohexyl)-4-hydroxyphenyl)ethenyl]benzoic acid;
Ethyl 4-[(E)-2-(3-(1-methylcyclohexyl)-4-(6-tert-butoxycarbonylpentyloxy)phenyl)ethenyl]benzoate;
Ethyl 4-[(E)-2-(3-(1-methylcyclohexyl)-4-(6-carboxypentyloxy)phenyl)ethenyl]benzoate;
4-[(E)-2-(3-(1-adamantyl)-4-hydroxyphenyl)ethenyl]benzoic acid;
Benzyl 6-[3-(1-adamantyl)-4-(1,2-dihydroxyethyl)-phenyl]-2naphthoate;
6-[3-(1-Adamantyl)-4-(1,2-dihydroxyethyl)phenyl]-2-naphthoic acid;
Benzyl 6-[3-(1-adamantyl)-4-(3-hydroxypropyl)phenyl]-2-naphthoate;
6-[3-(1-Adamantyl)-4-(3-hydroxypropyl)phenyl]-2-naphthoic acid;
Benzyl 6-[3-(1-adamantyl)-4-(3-acetoxypropyl)phenyl]-2-naphthoate;
6-[3-(1-Adamantyl)-4-(3-acetoxypropyl)phenyl]-2-naphthoic acid;
Benzyl 6-[3-(1-adamantyl)-4-(2,3-dihydroxypropyl)phenyl]-2-naphthoate;
6-[3-(1-Adamantyl)-4-(2,3-dihydroxypropyl)phenyl]-2-naphthoic acid;
N-methoxycarbonylmethyl-4-(6-benzyloxycarbonylnaphthyl)-2-(1-adamantyl)-phenylcarboxamide;
N-methoxycarbonylmethyl-4-(6-carboxynaphthyl)-2-(1-adamantyl)phenylcarboxamide;
6-[3-(1-Adamantyl)-4-N,N-dimethylcarbamoyl)phenyl]-2-naphthoic acid;
Benzyl 6-[3-(1-adamantyl)-4-(2(R), 3-dihydroxypropyloxy)phenyl]-2-naphthoate;
6-[3-(1-Adamantyl)-4-(2(R), 3-dihydroxypropyloxy)phenyl]-2-naphthoic acid;
6-[3-(1-Adamantyl)-4,5-methylenedioxyphenyl]-2-naphthoic acid;
N-ethyl 6-[3-(1-adamantyl)-4-methoxycarbonylphenyl]-2-naphthylcarboxamide;
N,N-morpholyl 6-[3-(1-adamantyl)-4-methoxycarbonylphenyl]-2-naphthylcarboxamide;
4-[(E)-2-(3-tert-butyl-4-methoxyphenyl)propenyl]phenyl carbinol; and
4-(E)-2-(3-tert-butyl-4-methoxyphenyl)propenyl]benzylacetate.

* * * * *